US008058462B2

(12) United States Patent
Powell et al.

(10) Patent No.: US 8,058,462 B2
(45) Date of Patent: *Nov. 15, 2011

(54) LIGAND MODIFIED POLY OXO-HYDROXY METAL ION MATERIALS, THEIR USES AND PROCESSES FOR THEIR PREPARATION

(75) Inventors: Jonathan Joseph Powell, Cambridge (GB); Sylvaine Francoise Bruggraber, Cambrigeshire (GB); Nuno Jorge Rodrigues Faria, Bedford (GB); Dora Isabel Amaral Pereira, Cambridge (GB)

(73) Assignee: Medical Research Council, Swindon (GB)

( * ) Notice: Subject to any disclaimer, the term of this patent is extended or adjusted under 35 U.S.C. 154(b) by 755 days.

This patent is subject to a terminal disclaimer.

(21) Appl. No.: 12/026,861

(22) Filed: Feb. 6, 2008

(65) Prior Publication Data

US 2008/0188555 A1 Aug. 7, 2008

Related U.S. Application Data

(60) Provisional application No. 60/888,386, filed on Feb. 6, 2007.

(30) Foreign Application Priority Data

Feb. 6, 2007 (GB) .................................. 0702270.0

(51) Int. Cl.
*C07F 15/00* (2006.01)
*A61K 31/295* (2006.01)
(52) U.S. Cl. ....................................... 556/138; 514/502
(58) Field of Classification Search .................. 556/138; 514/502

See application file for complete search history.

(56) References Cited

U.S. PATENT DOCUMENTS

| 2,575,347 | A | 11/1951 | Kumins et al. |
| 3,076,798 | A | 2/1963 | Mueller et al. |
| 3,679,377 | A | 7/1972 | Young et al. |
| 3,821,192 | A | 6/1974 | Montgomery et al. |
| 4,137,359 | A | 1/1979 | Bak et al. |
| 4,162,986 | A | 7/1979 | Alkaitis et al. |
| 5,514,281 | A | 5/1996 | Boos et al. |
| 7,943,664 | B2 * | 5/2011 | Powell et al. ............... 514/502 |
| 2003/0049284 | A1 | 3/2003 | Boccio et al. |
| 2003/0181320 | A1 * | 9/2003 | Rose et al. ................... 502/170 |
| 2005/0209187 | A1 | 9/2005 | Newton et al. |
| 2005/0209322 | A1 | 9/2005 | Rangisetty et al. |
| 2006/0205691 | A1 | 9/2006 | Geisser et al. |
| 2010/0032374 | A1 | 2/2010 | Powell et al. |

FOREIGN PATENT DOCUMENTS

| DE | 20 2005 014 332 U | 2/2006 |
| GB | 959282 | 8/1964 |
| GB | 1600449 | 10/1981 |
| NL | 264270 | 6/1964 |
| WO | 03031635 | 4/2003 |
| WO | 03092674 | 11/2003 |
| WO | 03097627 | 11/2003 |
| WO | 2004050031 | 6/2004 |
| WO | 2004074444 | 9/2004 |
| WO | 2004074444 A2 | 9/2004 |
| WO | 2005000210 | 1/2005 |
| WO | 2006037449 | 4/2006 |
| WO | 2008096130 A1 | 8/2008 |
| WO | 2009062993 A1 | 5/2009 |

OTHER PUBLICATIONS

Y. Maeda et al., "Correlation between Detrapped Valence States and Molecular Packing of Mixed-Valence Dinuclear Iron (II,III) Complexes of a Septadentate Polypyridine Ligand", Chemistry Letters, 1:65-66 (1995).
R.B. Lanjewar et al., "Quadrupole Hyperfine Interaction in Iron (III) Dicarboxylic Acid Complexes", J. Radioanalytical and Nuclear Chemistry, 125(1): 75-84 (1988).
Z. Smekal et al., "Binuclear iron (III)-iron (III) complexes with the tetradentate Schiff base, N,N'-bis(salicylidene) ethylenediamine and dicarboxylic acids or dithiooxamide as bridging ligands", Transition Met. Chem., 21: 49-51 (1996).
C.L. Sharma et al., Mossbauer Studies on Some Penta Coordinated Mixed Ligand Complexes of Iron (III), Chemica Scripta, 18(3): 133-134 (1981).
M. Bobtelsky et al., "The Structure and Behavior of Ferric Tartrate and Citrate Complexes in Dilute Solutions", Journal of the American Chemical Society, 69: 2286-2290 (1947).
V.R. Edgerton et al., "Iron-deficiency anaemia and its effect on worker productivity and activity patterns", British Medical Journal, 2:1546-1549 (1979).
P. Geisser et al., "Pharmacokinetics of Iron Salts and Ferric Hydroxide-Carbohydrate Complexes", Arzneimittelforshung/Drug Research, 37(1): 100-104 (1987).
A.F. Goodard et al., "Guidelines for the management of iron deficiency anaemia", BSG Guidelines in Gastroenterology, 2005.
R.S.J. Harvey et al., "Ferric trimaltol corrects iron deficiency anaemic in patients intolerant of iron", Aliment Pharmacol. Ther., 12: 845-848 (1998).
H.C. Heinrich, "Bioavailability of Trivalent Iron in Oral Iron Preparations", Arzneimittelforshung/Drug Research, 25(3): 420-426 (1975).
S. Hercberg et al., "Iron deficiency in Europe", Public Health Nutrition, 4(2B): 537-545 (2001).
R. Jugdaohsingh et al., "Rapid non-equilibrium aluminum-ligand interactions: studies on the precipitation of aluminum by laser light scattering, ultrafiltration and centrifugation", J. Inorg. Biochem., 87: 29-35 (2001).

(Continued)

*Primary Examiner* — Porfirio Nazario Gonzalez
(74) *Attorney, Agent, or Firm* — Patrick J. Hagan; Dann, Dorfman, Herrell and Skillman, P.C.

(57) ABSTRACT

Ligand-modified poly oxo-hydroxy metal ion materials and their uses are disclosed, in particular for nutritional, medical, cosmetic or biologically related applications for example for the treatment of a deficiency related to a component of the material or for the removal of an endogenous substance capable of binding to the material. The present invention further relates to processes for preparing the materials and optimising their physico-chemical properties and their medical uses.

69 Claims, 17 Drawing Sheets

OTHER PUBLICATIONS

R. Jugdaohsingh et al., "A rapid non-equilibrium critical precipitation assay to assess aluminum-ligand interactions", Chemical Speciation and Bioavailability, 16(3): 87-96 (2004).

J.P. Kaltwasser et al., "Bioavailability and Therapeutic Efficacy of Bivalent and Trivalent Iron Preparations", Arzneimittelforshung/Drug Research, 37(1a): 122-129 (1987).

P. Nielsen et al., "Bioavailability of Iron from Oral FErric Polymaltose in Humans", Arzneimittelforshung/Drug Research, 44(1): 743-748 (1994).

J. Powell et al., "Application of the critical preparation assay to complex samples: aluminum binding capacity of human gastrointestinal fluids", Chemical Speciation and Bioavailability, 16(3): 97-104 (20040.

F. Smith et al., "Serum Iron Determination Using Ferene Triazine", Clinical Biochemistry, 17: 306-310 (1984).

B.D. Scholz et al. "Anaemia is associated with reduced productivity of women workers even in less-physically-strenuous tasks", British Journal of Nutrition, 77(1): 47-57 (1997).

A.F. Hollerman et al., "Luhrbuch der Anorganischen Chemie", Berlin, Walter de Gruyter, DE, pp. 930-931 (1976).

A.F. Hollerman et al., "Luhrbuch der Anorganischen Chemie", Berlin, Walter de Gruyter, DE, pp. 929 (1995).

Jerome Rose et al., "Synthesis and Characterization of Carboxylate-FeOOH Nanoparticles (Ferroxanes) and Ferroxane-Derived Ceramics", Chem. Mater., 14: 621-628 (2002).

* cited by examiner

Figure 2: Effect of the ligand on the evolution of precipitation of the solid ferric oxo-hydroxide materials with increasing pH as described in titration protocol: no ligand (○), tartaric acid (■) and malic acid (▲). All were prepared in 50mM MOPS and 0.9% w/v NaCl.

A

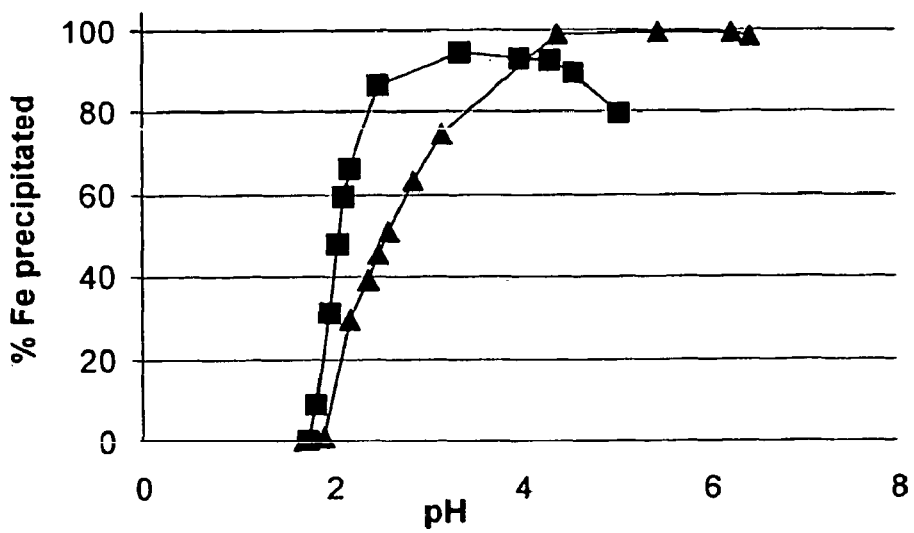

B

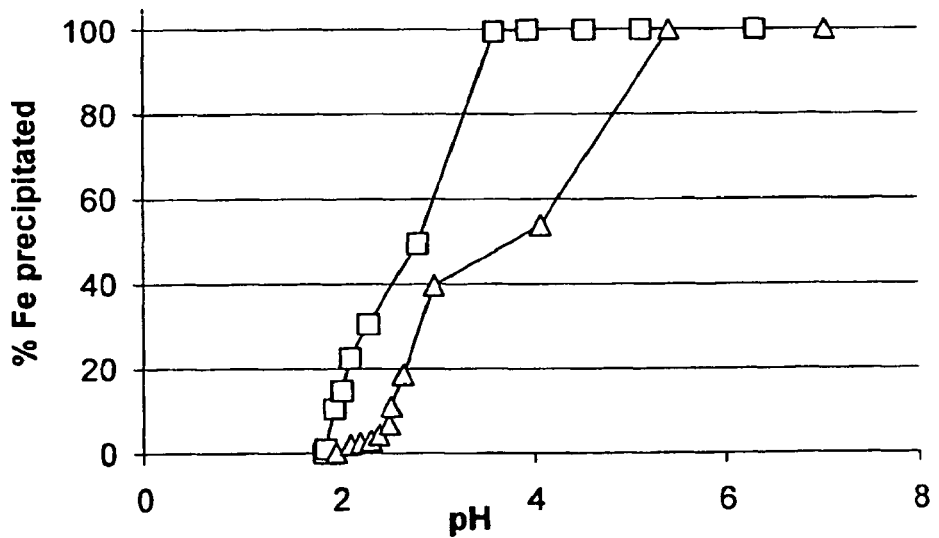

Figure 6: Example of the effect of the buffer (ligand B) on the evolution of precipitation of the solid ferric oxo-hydroxide materials with increasing pH in presence of tartaric acid at M:L ratio 4:1 (A) and without ligand A (B), in either 50mM adipic acid (squares) or 50mM MOPS (triangles). All titrations were performed following the protocol described in the methods and in the absence of electrolyte.

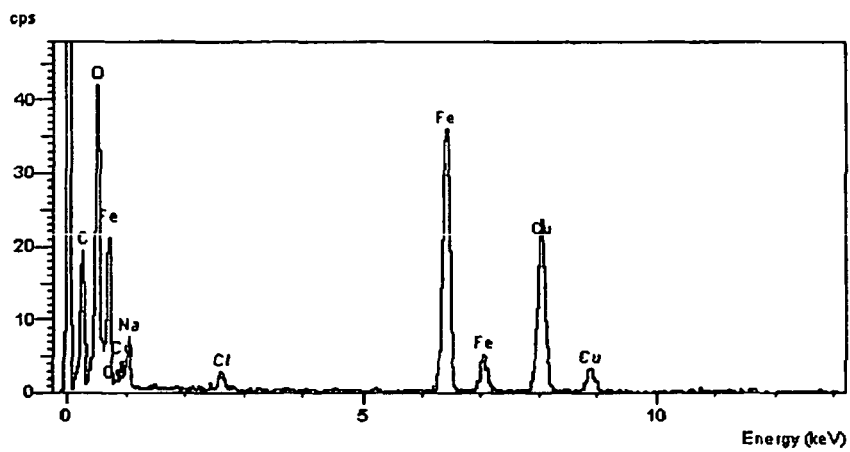
Figure 8. Energy dispersive X-ray analysis (EDX) of a ligand-modified poly oxo-hydroxy metal ion material (FeOHT-4:1-Ad20) showing the composition of the material to be predominantly Fe and O with incorporation of C plus very small additions of Na and Cl from the electrolyte used (the Cu signal is due to the support grid).

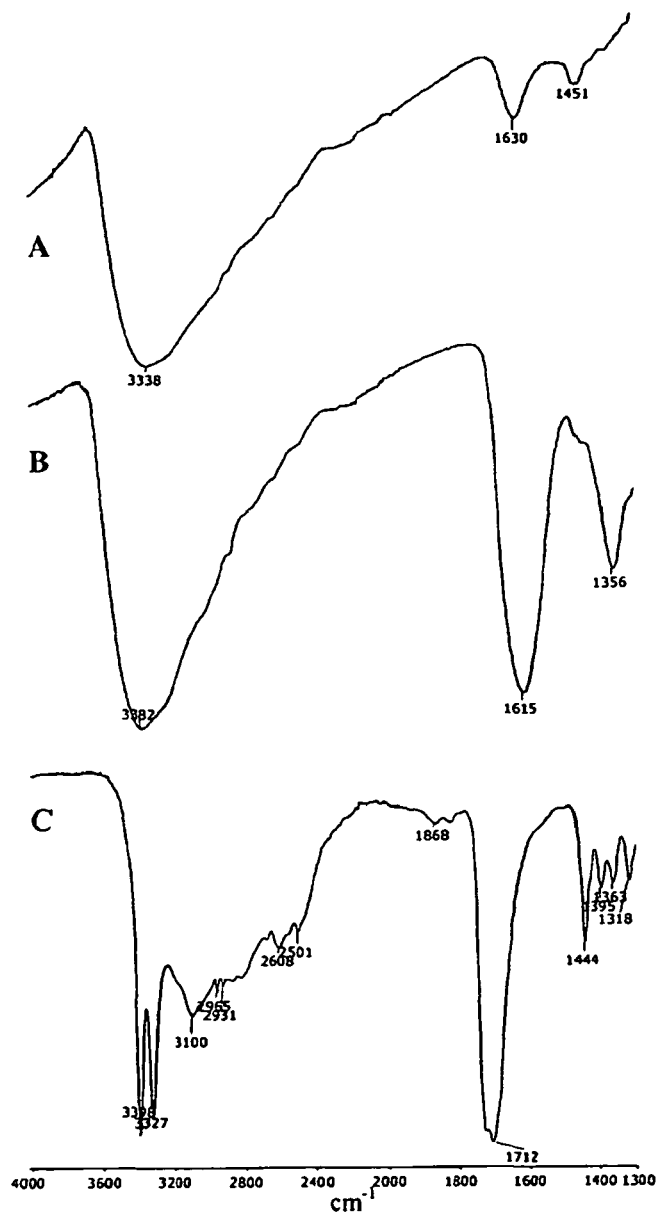

Figure 9. Typical infrared spectra of solid phase ferric oxo-hydroxide in (A), the tartrate-modified ferric oxo-hydroxide in (B) (i.e. the ligand-modified poly oxo-hydroxy metal ion material; FeOHT-4:1) and tartaric acid in (C). The band corresponding to the C=O stretch of tartaric acid (1712 $cm^{-1}$ in spectrum C) is replaced by two bands (1315 and 1615 $cm^{-1}$ in spectrum B) showing the presence of bonding between the carboxylate group of tartaric acid and iron in the FeOHT-4:1 material. Note also the presence of a broad band circa 3350 $cm^{-1}$ due to -OH stretch in spectra A and B.

A

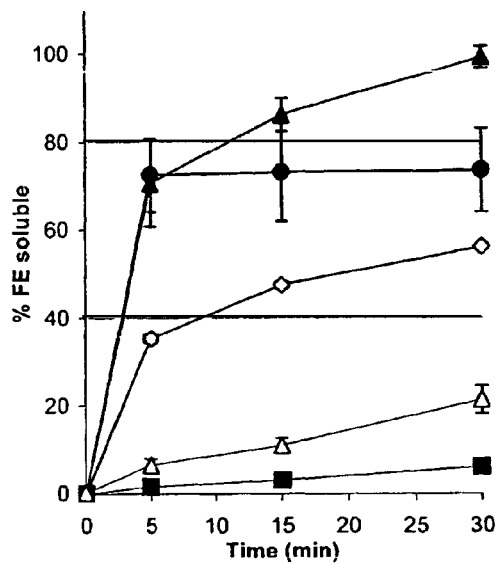

B

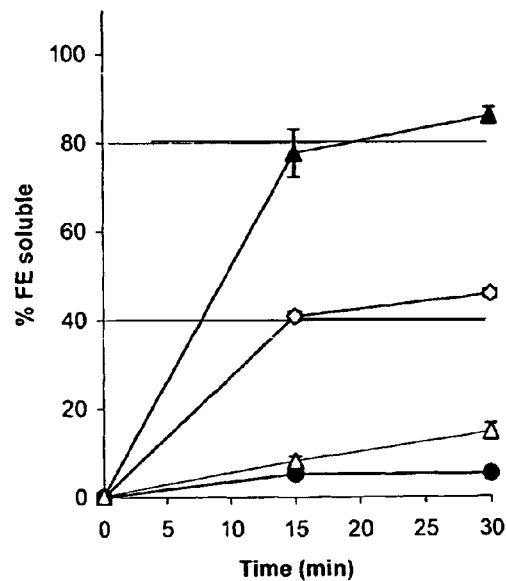

Figure 10. Percentage of 'soluble' iron after simulated passage through the stomach without (A) and with (B) ultrafiltration. Prior art is shown in closed symbols, namely ferric oxo-hydroxide (closed squares), Maltofer (closed circles), ferrous sulphate (closed triangles). The ligand-modified poly oxo-hydroxy metal ion materials are shown in open symbols, namely FeOHT-3:1-Ad20 (open diamonds) and FeOHM-4:1-Bic25 (open triangles). Note that certain error bars are too small to be visible.

A
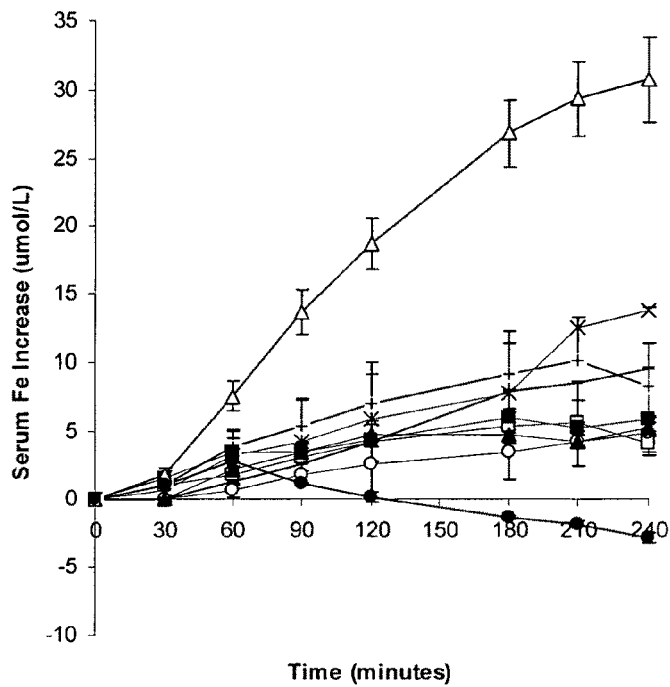
B
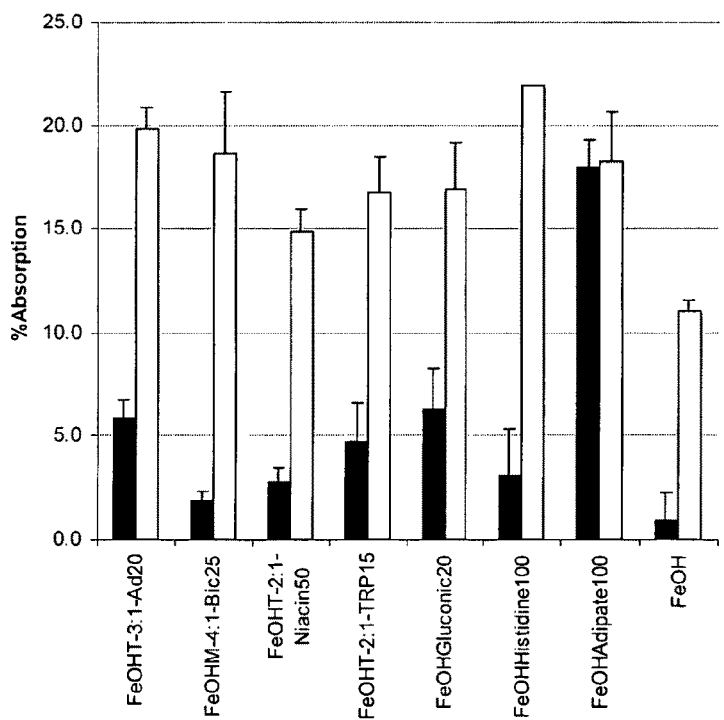
Figure 13

A

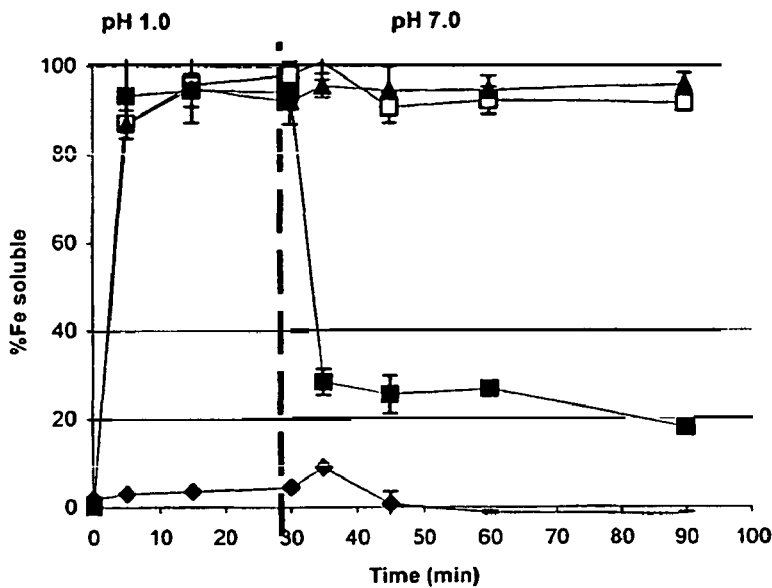

B

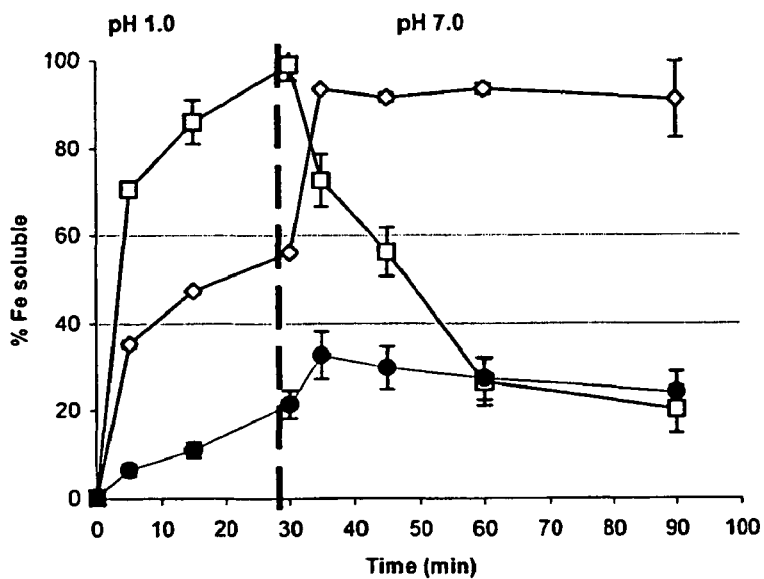

Figure 14: Dissolution rate of iron during the simulated passage through the stomach and duodenum from (A) prior art compounds: ferric pyrophosphate (Closed diamond), ferric chloride (Closed square), ferric tri-maltol (Closed triangle), ferrous bisglycinate (Open square); and (B) compounds tested in our *in vivo* study: ferrous sulphate (Open square), FeOHT3:1Ad20 (Open diamond) and FeOHM4:1Bic25 (Closed circle). For details of the protocol see 'simulated gastric dissolution rate' in the methods.

A
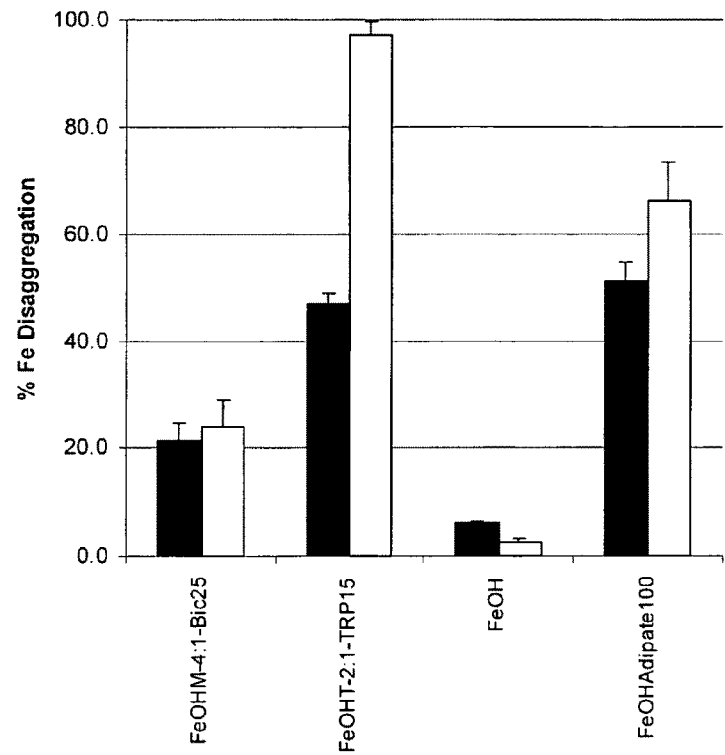
B
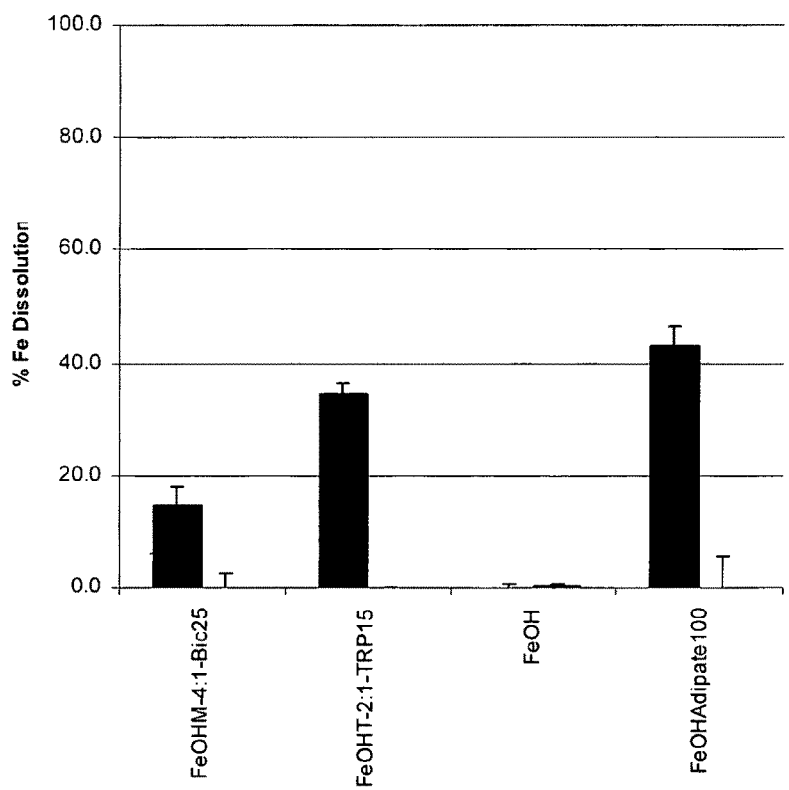
Figure 15

LIGAND MODIFIED POLY OXO-HYDROXY METAL ION MATERIALS, THEIR USES AND PROCESSES FOR THEIR PREPARATION

CROSS-REFERENCE TO RELATED APPLICATIONS

The present application claims the benefit of U.S. Provisional Patent Application No. 60/888,386, filed Feb. 6, 2007, the entire disclosure of which is incorporated by reference herein.

FIELD OF THE INVENTION

The present invention relates to ligand-modified poly oxo-hydroxy metal ion materials and their uses, in particular for nutritional, medical, cosmetic or biologically related applications for example for the treatment of a deficiency related to a component of the material or for the removal of an endogenous substance capable of binding to the material. The present invention further relates to processes for preparing the materials and optimising their physico-chemical properties and their medical uses.

BACKGROUND OF THE INVENTION

Iron deficiency is the most common micronutrient deficiency in the world today, affecting more than 4 billion people globally. It is estimated that 2 billion people—over 30% of the world's population—are anaemic (WHO, http://www-.who.int/nut/ida.htm, accessed 20 Dec. 2005). Iron deficiency is not a problem solely confined to the developing world. Epidemiological surveys performed in European countries show that iron deficiency concerns 10-30% of menstruating women and iron deficiency anaemia (IDA) 1.5 to 14% (Hercberg et al., 2001; Goddard et al., 2005). Iron deficiency anaemia can result in decreased intellectual performance, decreased physical capacity, alterations in temperature regulation, alterations in the development of gestation, and compromised immune and metabolic functions, all of which impact upon quality of life and health economics (Edgerton et al, 1979; Hercberg et al, 2001; Scholz et al, 1997). The standard first line treatment for simple mild IDA is, commonly, supplementation with oral ferrous sulphate. More complex or severe iron deficiencies may be treated with intravenous iron or blood transfusions, but subsequent management is with oral iron preparations. In spite of the widespread use of oral iron preparations their effectiveness is poor. This is due to: (i) variable absorption characteristics and (ii) side effects resulting in poor compliance. Strategies for the prevention of iron deficiency include the use of iron-fortified foods. Commonly used fortificants include ferrous sulphate, ferric chloride, ferric sodium EDTA and ferric pyrophosphates. However, despite fortification strategies, iron deficiency remains a common global problem and, thus, cheap and effective supplements are required.

WO 2005/000210 describes the synthesis of high molecular weight iron saccharidic complexes formed when freshly precipitated iron hydroxides are subsequently aggregated with sugar molecules to form secondary complexes. These complexes are acknowledged to be agglomerated mixtures.

WO 03/031635 relates to an enzymatic method to prepare calcium gluconate where the crystals are high purity and high solubility.

US 2005/0209322 describes a process for making sodium ferric gluconate complexes for i.v. iron administration that requires the initial step of preparing ferric hydroxide with a subsequent step of reacting with the ligand, sodium gluconate. US 2005/0209187 relates to a similar process for making iron sucrose complexes rather than iron gluconate complexes.

US 2003/0049284 describes a method for increasing the solubility of salts of alpha hydroxy carboxylic acids, by reaction with an alpha amino acid, such that the material would have improved nutritional supplementation properties.

U.S. Pat. No. 3,679,377 relates to the provision of an agronomically effective source of iron in a plant nutrient solution as a soluble ferric sulfato-hydroxyl complex anion. The materials produced are conventional ligand-metal ion complexes.

DE 20 2005 014332 U1 discloses metal-organic nanopowders for use in materials engineering such as the formation of polymeric composites through injection spraying or coating of the nanopowders into or onto an existing material.

Jugdaohsingh et al. (2004) describes a critical precipitation assay that utilises a solution phase reaction in which, at peri-neutral pH, organic acids compete with the formation of the oxo-bridges between aluminium atoms in the polymerisation process, limiting the growth and decreasing the branching of the polyhydroxy aluminium species (Jugdaohsingh et al. (2004); Powell et al. (2004)). The assay is usable because the efficiency of the ligand in interrupting this process is related to its affinity for aluminium. It was also noted in this work that during solution-phase growth of polyhydroxy aluminium species, the 'competing ligand' becomes incorporated within the polymer.

SUMMARY OF THE INVENTION

Broadly, the present invention relates to processes for preparing solid ligand-modified poly oxo-hydroxy metal ion materials and optimising their physico-chemical properties. The compositions generally comprise solid ligand-modified poly oxo-hydroxy metal ion materials represented by the formula $(M_xL_y(OH)_n)$, wherein M represents one or more metal ions, L represents one or more ligands and OH represents oxo or hydroxy groups, and may be used in nutritional, medical, cosmetic or other biologically relevant applications. These include delivery of the materials per se, or the use of the materials for the delivery of a component of the material, such as the metal ion, as a supplement or fortificant or food additive, or the use of the material to remove or inhibit a component and ameliorate any undesirable effects that it may cause.

The solid ligand-modified poly oxo-hydroxy metal ion materials disclosed herein constitute new forms of matter that have not been described previously in the art for such uses and which can be defined, inter alia, with reference to structural, spectroscopic or compositional parameters (i.e. using the analytical signatures of the materials) or by the processes by which the materials have been obtained. Thus, while metal oxo-hydroxide powders are very well known in the field of inorganic chemistry, in the present invention they are modified by biologically compatible ligands (i.e. other than oxo or hydroxy groups) to alter their physical and/or chemical properties to produce new materials and for use in new applications. As part of the unique processes used to optimise and produce the materials, it is notable that (i) the materials are recovered as a solid following precipitation from solution (e.g. aqueous solution) and (ii) that the ligand incorporation into the poly oxo-hydroxy metal ion solid phase is, for at least one of the ligands involved, through formal, identifiable bonding.

Thus, by way of example, the present invention differs from the critical precipitation assay disclosed in Jugdaohsingh et al. (2004) because that assay was carried out in solution and the precipitated material was not subsequently isolated or further employed. In contrast, in the present invention, the formation of the polymers continues to the point of precipitation and it is the solid materials that are then characterised and used in a variety of applications. Furthermore, the present inventors have found that the dried solid phase materials exhibit physico-chemical properties that are sensitively dependent upon the exact solution conditions used in the production of the material, for example the choice of ligand(s) and their concentration versus that of the metal ion. These materials are not, as might be expected, simply metal oxides/hydroxides with subtly differing degrees of crystallisation, and therefore subtly differing material properties, but instead the ligand(s) incorporate within the matrix of the poly oxo-hydroxy metal ion precipitate through substitution of oxo or hydroxyl groups. This is generally non-stoichiometric but, nonetheless, occurs through formal bonding, and leads to distinct and novel alterations in the chemistry, crystallinity and material properties of the solid. Thus, the compositions produced according to the present invention are chemically novel entities and are not simply the results of altering the degree of crystallinity of the metal oxides/hydroxides. Surprisingly, the conditions of precipitation do not easily predict the properties of the solid, such as the conditions of its re-dissolution and, for example, using this system it is perfectly possible to precipitate a material at pH 7 which can also be completely re-aquated at pH 7 using only a slightly larger volume of solution or by making a subtle change to the solution chemistry. Nonetheless, under the exact same reaction conditions, material is formed with highly reproducible properties. Thus, the idea underlying the present invention is that this process can be used to produce M:L:OH solids with precisely tailored physico-chemical characteristics for multiple biological applications such as in medicine, nutrition or cosmetics, where specific material characteristics are required. This approach has not been previously disclosed and it is surprising that such subtle changes in the precipitation process allow suitable changes in the solid phase that can be used to produce such precisely tailored physico-chemical (e.g. dissolution) characteristics or properties.

Accordingly, in a first aspect, the present invention provides a process for producing a solid ligand-modified poly oxo-hydroxy metal ion material ($M_xL_y(OH)_n$), wherein M represents one or more metal ions, L represents one or more ligands and OH represents oxo or hydroxy groups, and wherein the gross solid ligand-modified poly oxo-hydroxy metal ion material has one or more reproducible physico-chemical properties and displays M-L bonding for at least one ligand that can be detected by physical analytical techniques, the process comprising:
(a) mixing the metal ions M and the ligands L at a first pH(A) at which the components are soluble;
(b) changing the pH(A) to a second pH(B) to cause a solid precipitate of the solid ligand-modified poly oxo-hydroxy metal ion material to be formed; and
(c) separating, and optionally drying, the solid ligand-modified poly oxo-hydroxy metal ion material produced in step (b).

By way of example, the materials produced by the processes of the present invention may be employed in nutritional, medical, cosmetic or other biologically relevant applications. A preferred example of such an application is the use of the material to deliver the material, or a part thereof such as a metal ion or a ligand, to a subject, for example to correct a deficiency in the component or so that the component provide a beneficial effect to the subject. An alternative example is the use of a material to bind or sequester a component that may be present in the system into which the material is introduced, thereby to remove or inhibit that component and ameliorate any undesirable effects that it may cause. In view of this, the process may comprise the further step of formulating the solid ligand-modified poly oxo-hydroxy-metal ion material in a composition for administration to a subject.

In any aspect of the present invention, the processes disclosed herein may be employed to engineer or optimise the physico-chemical properties of the material, for example to control the dissolution profile or the adsorption profile, or a similar property of the material, and it is a considerable advantage of the processes described herein that they are highly amenable to such optimisation studies.

Accordingly, in a further aspect, the present invention provides a process for producing a solid ligand-modified poly oxo-hydroxy metal ion material and optimising a desired physico-chemical property of the material to adapt it for a nutritional, medical, cosmetic or biologically related application, wherein the solid ligand-modified poly oxo-hydroxy metal ion material is represented by the formula ($M_xL_y(OH)_n$), wherein M represent one or more metal ions, L represents one or more ligands and OH represents oxo or hydroxy groups, wherein the gross solid ligand-modified poly oxo-hydroxy metal ion material has one or more reproducible physico-chemical properties and displays M-L bonding for at least one ligand that can be detected by physical analytical techniques, the process comprising:
(a) mixing the metal ion(s) M and the ligand(s) L in a reaction medium at a first pH(A) at which the components are soluble;
(b) changing the pH(A) to a second pH(B) to cause a solid precipitate of the ligand-modified poly oxo-hydroxy metal ion material to be formed;
(c) separating, and optionally drying, the solid ligand-modified poly oxo-hydroxy metal ion material produced in step (b).
(d) testing the desired physico-chemical characteristic(s) of the precipitated solid ligand-modified poly oxo-hydroxy metal ion material; and
(e) repeating steps (a) to (d) as required by varying one or more of:
(i) the identity or concentration of the metal ion(s) (M) and/or the ligand(s) (L) supplied in step (a); and/or
(ii) the ratio of metal ion(s) (M) to ligand(s) (L) supplied in (a); and/or
(iii) pH(A); and/or
(iv) pH(B); and/or
(v) the rate of change from pH(A) to pH(B); and/or
(vi) the presence or concentration of a buffer
thereby to produce a solid ligand-modified poly oxo-hydroxy metal ion material having the desired physico-chemical property.

Examples of possible metal ions and ligands are provided below. In some embodiments, the materials of the present invention may employ more than one species of metal ion or ligand, for example two, three, four or five different species of metal ion or ligand. In addition, in some embodiments, the ligand(s) L may also have some buffering capacity as described in more detail below.

As part of the process for optimising a desired physico-chemical property of the material to provide for its application, it may be desirable to vary physical or chemical reaction conditions used in the process for making the solid ligand-modified poly oxo-hydroxy metal ion material, for example the temperature of the reaction, the ionic content and strength of the solution, buffering capacity of the solution (e.g. using a buffer such as MOPS as in the examples), or the conditions and apparatus used to mix the reactants, to determine whether and how this affects one or more properties of the material.

In a further aspect, the present invention provides a process for making solid ligand-modified poly oxo-hydroxy metal ion materials for administration to a subject, the process comprising having optimised a solid ligand-modified poly oxo-hydroxy metal ion material according to the process as disclosed herein, the further step of manufacturing the solid ligand-modified poly oxo-hydroxy metal ion material in bulk and/or formulating it in a composition.

In one embodiment, the processes of the present invention have been employed by way of example to optimise and produce ferric iron compositions, e.g. for use as iron supplements, fortificants or therapeutics. As is generally used in the art, supplements are nutritional compositions that are taken by subjects to correct, prevent or insure against a deficiency in a mineral or other dietary component. A fortificant is somewhat similar to a supplement but is generally applied to compositions that are added routinely to foodstuffs to improve their nutritional value, for example the addition of iodide to table salt, B group vitamins to breakfast cereals or iron to cereal products. In addition, compositions may be used therapeutically, usually in the context of preventing or treating a pathology or condition caused by the deficiency in a mineral or other dietary component. In the case of iron, the ferric iron compositions disclosed herein may be employed as supplements, fortificants or as therapeutic compositions, for example in the treatment of iron deficiency in pregnant or pre-menopausal women, cancer or inflammatory disease. Such therapeutics are typically administered orally or intravenously.

Accordingly, in one aspect, the present invention further provides a ferric iron composition for administration to a subject which comprises a solid ligand-modified poly oxo-hydroxy metal ion material represented by the formula $(M_xL_y(OH)_n)$, wherein M represents one or more metal ions that comprise $Fe^{3+}$ ions, L represents one or more ligands and OH represents oxo or hydroxy groups in which the ligands L are substantially randomly substituted for the oxo or hydroxy groups, the solid ligand-modified poly oxo-hydroxy metal ion material having one or more reproducible physico-chemical properties and demonstrable M-L bonding using physical analysis.

Generally a useful dietary iron supplement needs to share some characteristics of simple ferrous salts, namely cost relatively little and be reasonably well absorbed, but at the same time, be less redox active and hence lead to a low incidence of side-effects. Some ferric salts do not suffer from this disadvantage as they are already oxidised, and are therefore less prone to redox activity because the initiation of iron reduction in the gastrointestinal lumen is less favourable than the initiation of iron oxidation. Moreover, the controlled mucosal reduction of ferric iron, via the mucosal protein DcytB, may provide a rate-limiting step for the entry of iron to the circulation, which would lower the production of circulating non-transferrin bound iron (NTBI). NTBI may lead to oxidative damage in the circulation, endothelium and the more vascular organs. However, simple ferric salts are not efficient supplements because their rapid dissolution in the stomach is followed by concentration-dependent oxo-hydroxy polymerisation in the small bowel which inhibits their absorption. Thus, while ferric iron salts, typically ferric chloride, have been tried as fortificants in certain foods, these are poorly absorbed at supplemental or therapeutic doses due to uncontrolled delivery of ferric ions into the small bowel at bolus doses. Chelation of ferric iron, for example with maltol, may help overcome this small bowel solubility issue for bolus doses, but has not proven commercially viable due to production costs (WO 03/097627). In addition there are concerns over the safety of chelators such as maltol. The compositions disclosed herein are engineered to overcome such absorption, safety, side effect and production cost problems. Thus, these solid ligand-modified poly oxo-hydroxy metal ion materials can be tailored to have distinct dissolution profiles in the stomach environment compared to the small bowel environment. In this way, rapid dissolution in the stomach that then leads to undesirable bolus delivery of iron in the small bowel, as occurs for simple ferrous and ferric salts, can be avoided in the design of these materials. Both the pH of dissolution and the rate of dissolution can be engineered to match requirements. Potentially, these solid phase ligand-modified poly oxo-hydroxy ferric iron materials could be tailored to 'sense' iron requirements. Absorption of iron from the gut lumen and into the circulation occurs in individuals who require iron. In those who do not require iron there will be little or no absorption and more iron will remain in the lumen. The dissolution or disaggregation of these solid phase ligand-modified poly oxo-hydroxy ferric iron materials could be 'set' such that they dissolve or disaggregate efficiently in an environment that is low in aquated iron, but inefficiently in an environment that is high in aquated iron. This again would help to reduce side effects without compromising absorption in those who need iron. Whether these materials are designed to dissolve or disaggregate under gastrointestinal conditions depends upon the optimal mode of iron absorption in the gut as both soluble iron and very small aquated particulate iron could both be absorbed but, either way, the ligand-modified poly oxo-hydroxy ferric iron materials could be so designed.

In a further aspect, the present invention provides the use of a composition of a solid ligand-modified poly oxo-hydroxy metal ion material $(M_xL_y(OH)_n)$ as obtainable by the processes disclosed herein for the preparation of a medicament for therapeutic delivery of the metal ion to the subject. Alternatively, the present invention provides a solid ligand-modified poly oxo-hydroxy metal ion material $(M_xL_y(OH)_n)$ as obtainable by the processes disclosed herein for the delivery of the metal ion to a subject.

Examples of the uses of the solid ligand-modified poly oxo-hydroxy metal ion materials disclosed herein include, but are not limited to, uses as: dietary mineral supplements and fortificants; therapeutic mineral supplements (e.g. as administered by i.v. and oral routes); drugs, nutrients or cosmetic carriers/co-complexes; phosphate binding agents; other binding or sequestering applications; food additives; anti-perspirants; sun-protection agents; vaccine adjuvants; immuno-modulatory agents; direct cosmetic applications including exfoliating agents; bone and dental filler/cements; implant materials including brachytherapy, and imaging and contrast agents.

Embodiments of the present invention will now be described by way of example and not limitation with reference to the accompanying figures and examples.

BRIEF DESCRIPTION OF THE FIGURES

FIG. 6: Example of the effect of "ligand B" on the evolution of precipitation of the solid ligand-modified poly oxo-hydroxy metal ion material with increasing pH in presence (i) or absence (ii) of "ligand A", namely tartaric acid, at M:$L_A$ ratio 4:1. "Ligand B" showed were either 50 mM adipic acid (squares) or 50 mM MOPS (triangles). All titrations were performed following the protocol described in the methods and in the absence of electrolyte. The iron concentration in the initial solution (prior to precipitation) was 27 mM.

FIG. 8. Energy dispersive X-ray microanalysis (EDX) of a ligand-modified poly oxo-hydroxy metal ion material (FeOHT-3:1-Ad20) showing the composition of the material to be predominantly Fe and O with incorporation of C plus very small additions of Na and Cl from the electrolyte used (the Cu signal is due to the support grid).

FIG. 9. Typical infrared spectra of solid ferric oxo-hydroxide in (A), the tartrate-modified ferric oxo-hydroxide in (B) (i.e. the ligand-modified poly oxo-hydroxy metal ion material; FeOHT-4:1) and tartaric acid in (C). The band corresponding to the C=O stretch of tartaric acid (1712 $cm^{-1}$ in spectrum C) is replaced by two bands (1356 and 1615 $cm^{-1}$ in spectrum B) showing the presence of bonding between the carboxylate group of tartaric acid and iron in the FeOHT-4:1 material. Note also the presence of a broad band circa 3350 $cm^{-1}$ due to —OH stretch in spectra A and B.

FIG. 10. Percentage of iron disaggregation (without ultrafiltration, A) and dissolution (with ultrafiltration, B) after simulated passage through the stomach for the time indicated. Prior art is shown in closed symbols, namely ferric oxo-hydroxide (closed squares), Maltofer (closed circles), ferrous sulphate (closed triangles). The ligand-modified poly oxo-hydroxy metal ion materials are shown in open symbols, namely FeOHT-3:1-Ad20 (open diamonds) and FeOHM-4:1-Bic25 (open triangles). Error bars represent STDEV (note that certain error bars are too small to be visible).

FIG. 13: Examples of the serum iron increase (A) and percentage iron absorption (B) in human volunteers following ingestion of ferrous sulphate, ferric oxo-hydroxide or different solid ligand-modified poly oxo-hydroxy ferric materials. A: ferrous sulphate (open triangle, n=30); FeOHT-3:1-Ad20 (+ symbol, n=4); FeOHT-2:1-TRP15 (− symbol, n=4); FeOHAdipate100 (x symbol, n=2); FeOHHistidine100 (closed square, n=2); FeOHM-4:1-Bic25 (open square, n=3); FeOHGluconic20 (closed triangle, n=3); FeOHT-2:1-Niacin50 (open circle, n=3); FeOH (closed circle, n=2). B: Percentage iron absorption (calculated as the red blood cell incorporation of $^{58}Fe$ divided by 0.80) from ferric oxo-hydroxide or the solid ligand-modified poly oxo-hydroxy ferric materials (black bars) compared with estimated absorption of iron from ferrous sulphate for the same group of study participants (open bars). Error bars represent the SEM. Number of each pairing vary from 2 to 4, except for ferrous sulphate in the FeOHHistidine-100 group which was 1.

FIG. 14: Disaggregation of iron during simulated passage through the stomach and duodenum from (A) prior art compounds: ferric pyrophosphate (Closed diamond), ferric chloride (Closed square), ferric tri-maltol (Closed triangle), ferrous bisglycinate (Open square); and (B) a selection of compounds tested in our in vivo study in FIG. 13: ferrous sulphate (Open square), FeOHT-3:1-Ad20 (Open diamond) and FeOHM-4:1-Bic25 (Closed circle). For details of the protocol see In vitro gastrointestinal digestion assay in the Methods.

FIG. 15: Examples of the effect of different ligands, at differing M:L ratios, on the percentage of iron disaggregation (A) and on the percentage of iron dissolution (B) of solid ligand-modified poly oxo-hydroxy metal ion materials, after 30 minutes incubation at gastric pH 1.2 (black bars, n=3) or 60 minutes incubation at intestinal pH 7.0 (open bars, n=3); error bars represent standard deviations.

DETAILED DESCRIPTION

The Metal Ion (M)

Figure 1:
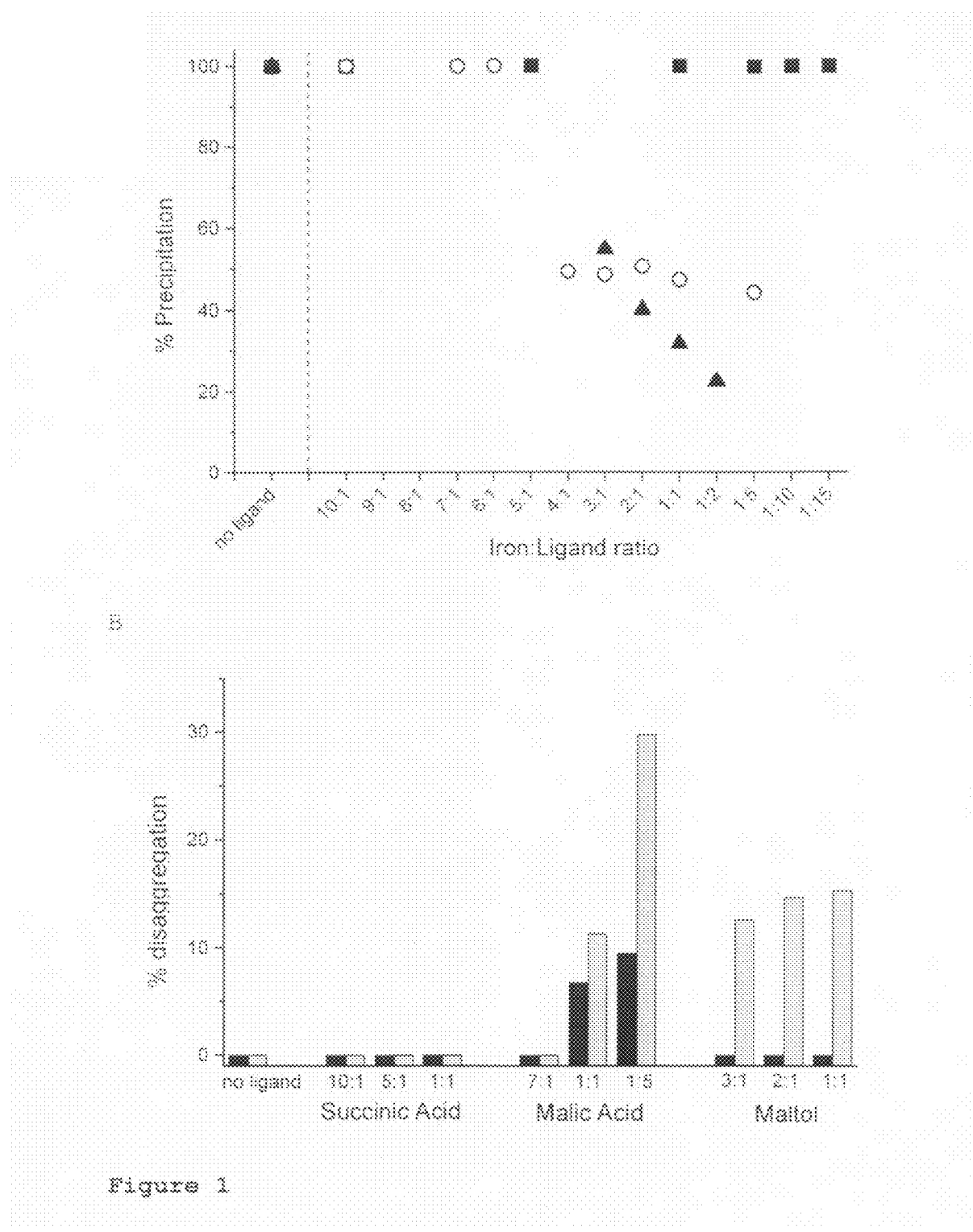
FIG. 1: Examples of the effects of weak (succinate, closed square), intermediate (malate, open circle) and strong (maltol, closed triangle) ligands on the formation of solid ligand-modified poly oxo-hydroxy metal ion material (A) and the disaggregation of the wet solid materials in buffers at pH 6 (black bars) and pH 4 (grey bars) (B), using the method described in "screening assay". The ratios indicated are M:L ratios that were selected for formation of the materials. The iron concentration in the initial solution (prior to precipitation) was 27 mM.

The solid ligand-modified poly oxo-hydroxy metal ion materials may be represented by the formula $(M_xL_y(OH)_n)$, where M represents one or more metal ions. Normally, the metal ion will originally be present in the form of a salt that in the preparation of the materials may be dissolved and then induced to form poly oxo-hydroxy co-complexes with ligand (L) some of which is integrated into the solid phase through formal M-L bonding, i.e. not all of the ligand (L) is simply trapped or adsorbed in the bulk material. The bonding of the metal ion in the materials can be determined using physical analytical techniques such as infrared spectroscopy where the spectra will have peaks characteristic of the bonds between the metal ion and the ligand (L), as well as peaks characteristic of other bonds present in the material such as M-O, O—H and bonds in the ligand species (L). Preferred metal ions (M) are biologically compatible under the conditions for which the materials are used and are readily precipitatable from aqueous solution by forming oxo-hydroxides. Examples of metal ions include iron, calcium, magnesium, zinc, copper, manganese, chromium and aluminium ions. A particularly preferred metal ion is ferric iron ($Fe^{3+}$).

By way of reference to the ferric iron compositions disclosed herein, the presence of formal bonding is one aspect that mainly distinguishes the materials from other products such as "iron polymaltose" (Maltofer) in which particulate crystalline iron oxo-hydroxide is surrounded by a sugar shell formed from maltose and thus is simply a mixture of iron oxo-hydroxide and sugar at the nano-level (Heinrich (1975); Geisser and Müller (1987); Nielsen et al (1994; U.S. Pat. No. 3,076,798); US20060205691). In addition, the materials of the present invention are metal poly oxo-hydroxy species modified by non-stoichiometric ligand incorporation and should therefore not be confused with the numerous metal-ligand complexes that are well reported in the art (e.g., see WO 03/092674, WO 06/037449). Although generally soluble, such complexes can be precipitated from solution at the point of supersaturation, for example ferric trimaltol, Harvey et al. (1998), WO 03/097627; ferric citrate, WO 04/074444 and ferric tartrate, Bobtelsky and Jordan (1947) and, on occasions, may even involve stoichiometric binding of hydroxyl groups (for example, ferric hydroxide saccharide, U.S. Pat. No. 3,821,192). The use of hydroxyl groups to balance the charge and geometry of metal-ligand complexes is, of course, well reported in the art (e.g. iron-hydroxy-malate, WO 04/050031) and unrelated to the solid ligand-modified poly oxo-hydroxy metal ion materials reported herein.

Without modification, the primary particles of the materials have metal oxide cores and metal hydroxide surfaces and within different disciplines may be referred to as metal oxides or metal hydroxides. The use of the term 'oxo-hydroxy' or 'oxo-hydroxide' is intended to recognise these facts without any reference to proportions of oxo or hydroxy groups. Hydroxy-oxide could equally be used therefore. As described above, the materials of the present invention are altered at the level of the primary particle of the metal oxo-hydroxide with at least some of the ligand L being introduced into the structure of the primary particle, i.e. leading to doping or contamination of the primary particle by the ligand L. This may be contrasted with the formation of nano-mixtures of metal oxo-hydroxides and an organic molecule, such as iron saccharidic complexes, in which the structure of the primary particles is not so altered.

The primary particles of the ligand-modified poly oxo-hydroxy metal ion materials described herein are produced by a process referred to as precipitation. The use of the term precipitation often refers to the formation of aggregates of materials that do separate from solution by sedimentation or centrifugation. Here, the term "precipitation" is intended to describe the formation of all solid phase material, including aggregates as described above and solid materials that do not aggregate but remain as non-soluble moieties in suspension, whether or not they be particulate, colloidal or sub-colloidal (nanoparticulates). These latter solid materials may also be referred to as aquated particulate solids.

In the present invention, reference may be made to the modified metal oxo-hydroxides having polymeric structures that generally form above the critical precipitation pH. As used herein, this should not be taken as indicating that the structures of the materials are polymeric in the strict sense of having a regular repeating monomer unit because, as has been stated, ligand incorporation is, except by co-incidence, non-stoichiometric. The ligand species is introduced into the solid phase structure by substituting for oxo or hydroxy groups leading to a change in solid phase order. In some cases, for example the production of the ferric iron materials exemplified herein, the ligand species L may be introduced into the solid phase structure by the substitution of oxo or hydroxy groups by ligand molecules in a manner that decreases overall order in the solid phase material. While this still produces solid ligand modified poly oxo-hydroxy metal ion materials that in the gross form have one or more reproducible physicochemical properties, the materials have a more amorphous nature compared, for example, to the structure of the corresponding metal oxo-hydroxide. The presence of a more disordered or amorphous structure can readily be determined by the skilled person using techniques well known in the art. One exemplary technique is X-ray diffraction (XRD) which will produce an X-ray diffraction pattern for the ferric iron materials exemplified herein having poorly identifiable peaks for L or MO/MOH, XRD relying on a regular arrangement of atoms to diffract the X-rays and produce a pattern. Alternatively or additionally, a decrease in the crystallinity of the structure of the material may be determined by high resolution transmission electron microscopy. High resolution transmission electron microscopy allows the crystalline pattern of the material to be visually assessed. It can indicate the primary particle size and structure (such as d-spacing) and give some information on the distribution between amorphous and crystalline material. Using this technique, it is apparent that the chemistry described above increases the amorphous phase of our described materials compared to corresponding materials without the incorporated ligand. This may be especially apparent using high angle annular dark field aberration-corrected scanning transmission electron microscopy due to the high contrast achieved while maintaining the resolution thus allowing the surface as well as the bulk of the primary particles of the material to be visualised.

The reproducible physico-chemical property or characteristic of the materials of the present invention will be dependent on the application for which the material is intended. Examples of the properties that can be usefully modulated using the present invention include: dissolution (rate, pH dependence and pM dependence), disaggregation, adsorption and absorption characteristics, reactivity-inertness, melting point, temperature resistance, particle size, magnetism, electrical properties, density, light absorbing/reflecting properties, hardness-softness, colour and encapsulation properties. Examples of properties that are particularly relevant to the field of supplements, fortificants and mineral therapeutics are physico-chemical properties selected from one or more of a dissolution profile, an adsorption profile or a reproducible elemental ratio. In this context, a property or characteristic may be reproducible if replicate experiments are reproducible within a standard deviation of preferably ±10%, and more preferably ±5%, and even more preferably within a limit of ±2%.

The dissolution profile of the solid ligand-modified poly oxo-hydroxy metal ion materials can be represented by different stages of the process, namely disaggregation and dissolution. The term dissolution is used to describe the passage of a substance from solid to soluble phase. More specifically, disaggregation is intended to describe the passage of the materials from a solid aggregated phase to an aquated phase that is the sum of the soluble phase and the aquated particulate phase (i.e. solution plus suspension phases). Therefore, the term dissolution as opposed to disaggregation more specifically represents the passage from any solid phase (aggregated or aquated) to the soluble phase.

Preferred specific examples of the metal ions (M) include, but are not restricted to, Groups 2, 3 and 5 metals of the periodic table, the transition metals, heavy metals and lanthanoids. Examples include, but are not restricted to: $Ag^{2+}$, $Al^{3+}$, $Au^{3+}$, $Be^{2+}$, $Ca^{2+}$, $Co^{2+}$, $Cr^{3+}$, $Cu^{2+}$, $Eu^{3+}$, $Fe^{3+}$, $Mg^{2+}$, $Mn^{2+}$, $Ni^{2+}$, $Sr^{2+}$, $V^{5+}$, $Zn^{2+}$, $Zr^{2+}$. Moreover, many of these metal cations take on different oxidation states so it will also be appreciated that these examples are not restricted to the oxidation states shown. In many cases, the solid ligand-modified poly oxo-hydroxy metal ion materials comprise a single species of metal ion, for example $Fe^{3+}$.

The Ligand (L)

In the solid phase ligand-modified poly oxo-hydroxy metal ion-species represented by the formula $(M_xL_y(OH)_n)$, L represents one or more ligands or anions, such as initially in its protonated or alkali metal form, that can be incorporated into the solid phase ligand-modified poly oxo-hydroxy metal ion material. Typically, this is done to aid in the modification of a physico-chemical property of the solid material, e.g. as compared to a poly oxo-hydroxylated metal ion species in which the ligand(s) are absent. In some embodiments of the present invention, the ligand(s) L may also have some buffering capacity. Examples of ligands that may be employed in the present invention include, but are by no means limited to: carboxylic acids such as adipic acid, glutaric acid, tartaric acid, malic acid, succinic acid, aspartic acid, pimelic acid, citric acid, gluconic acid, lactic acid or benzoic acid; food additives such as maltol, ethyl maltol or vanillin; 'classical anions' with ligand properties such as bicarbonate, sulphate and phosphate; mineral ligands such as silicate, borate, molybdate and selenate; amino acids such as tryptophan, glutamine, proline, valine, or histidine; and nutrient-based ligands such as folate, ascorbate, pyridoxine or niacin. Typically ligands may be well recognised in the art as having high affinity for a certain metal ion in solution or as having only low affinity or not be typically recognised as a ligand for a given metal ion at all. However, we have found that in poly oxo-hydroxy metal ion materials, ligands may have a role in spite of an apparent lack of activity in solution. Typically, two ligands of differing affinities for the metal ion are used in the production of these materials although one, two, three, four or more ligands may be useful in certain applications.

For many applications, ligands need to be biologically compatible under the conditions used and generally have one or more atoms with a lone pair of electrons at the point of reaction. The ligands include anions, weak ligands and strong ligands. Ligands may have some intrinsic buffering capacity during the reaction. Without wishing to be bound by a particular explanation, the inventors believe that the ligands have two modes of interaction: (a) substitution of hydroxy groups and, therefore, incorporation with a largely covalent character within the material and (b) non-specific adsorption (ion pair formation). These two modes likely relate to differing metal-ligand affinities (i.e. strong ligands for the former and weak ligands/anions for the latter). There is some evidence in our current work that the two types of ligand are synergistic in modulating dissolution characteristics of the materials and, perhaps, therefore, in determining other characteristics of the material. In this case, two ligand types are used and at least one (type (a)) is demonstrable as showing metal binding within the material. Ligand efficacy, probably especially for type (b) ligands, may be affected by other components of the system, particularly electrolyte.

The ratio of the metal ion(s) to the ligand(s) (L) is also a parameter of the solid phase ligand-modified poly oxo-hydroxy metal iron material that can be varied according to the methods disclosed herein to vary the properties of the materials. Generally, the useful ratios of M:L will be between 10:1, 5:1, 4:1, 3:1, 2:1 and 1:1 and 1:2, 1:3, 1:4, 1:5 or 1:10.

Hydroxy and Oxo Groups

The present invention may employ any way of forming hydroxide ions at concentrations that can provide for hydroxy surface groups and oxo bridging in the formation of these poly oxo-hydroxy materials. Examples include but are not limited to, alkali solutions such as sodium hydroxide, potassium hydroxide and sodium bicarbonate, that would be added to increase [OH] in an ML mixture, or acid solutions such as mineral acids or organic acids, that would be added to decrease [OH] in an ML mixture.

Conditions Used in the Process

The exact conditions of mixing and precipitation of the solid ligand-modified poly oxo-hydroxy metal ion material will vary depending upon the desirable characteristics of the solid material. Typical variables are:

(1) Starting pH (i.e. the pH at which M and L are mixed). This is always a different pH to that at which oxo-hydroxy polymerisation commences. Preferably, it is a more acidic pH, more preferably below a pH of 2.

(2) The pH at which oxo-hydroxy polymerisation commences. This is always a different pH to that of the starting pH. Preferably, it is a less acidic pH and most preferably above a pH of 2.

(3) Final pH. This will always promote precipitation and may promote agglomeration of the solid ligand-modified poly oxo-hydroxy metal ion material and preferably will be a higher pH than the pH at which oxo-hydroxy polymerisation commences. It will be appreciated by the skilled person that where a pH difference exists between commencement of oxo-hydroxy polymerisation and the final pH value, addition of further M, L, $OH^-$, $H^+$, excipients or other substances may be undertaken before the final pH value is achieved.

(4) Rate of pH change from commencement of oxo-hydroxy polymerisation to completion of reaction. This will occur within a 24 hour period, preferably within an hour period and most preferably within 20 minutes.

Concentrations of M and L. While the concentration of OH is established by the pH during oxo-hydroxy polymerisation, the concentrations of total M and total L in the system will be fixed by the starting amounts in the ML mix and the final solution volume. Typically, this will exceed $10^{-6}$ molar for both M and L and more preferably it will exceed $10^{-3}$ molar. Concentrations of M and L are independent and chosen for one or more desired characteristics of the final material and especially so that the concentration of M is not too high such that the rate of oxo-hydroxy polymerisation occurs too rapidly and prevents L incorporation. Similarly the concentration of L will not be too high to prevent metal oxo-hydroxy polymerisation. For example, the ligand-modified poly oxo-hydroxy materials in which M is ferric iron are produced preferably with iron concentrations of the initial solution below 300 mM and most preferably below 200 mM, providing ranges of ferric iron concentrations between 1 mM and 300 mM, more preferably between 20 mM and 200 mM, and most preferably of about 40 mM.

(5) Solution phase. The preferred solution for this work is aqueous and most preferably is water.

(6) Buffer. The solution may have a buffer added to help stabilise the pH range of oxo-hydroxy polymerisation. Buffers may be inorganic or organic, and in some embodiments will not be involved in formal bonding with the metal ion(s) M of the solid phase material. Alternatively, one or more of the ligands L involved in formal bonding with the metal ion(s) M of the solid phase material may have some buffering capacity that is additionally favourable in achieving the desired composition of the final material. Buffer concentrations are less than 500 mM, preferably less than 200 mM and most preferably less than 100 mM.

(7) Temperature. The preferred temperature is above 0 and below 100° C., typically between room temperature (20-30° C.) and 100° C., most typically at room temperature.

(8) Ionic strength. Electrolyte such as, but not limited to, potassium chloride and sodium chloride, may be used in the procedure. The ionic strength of the solution may thus range from that solely derived from the components and conditions outlined in (1)-(8) above or from the further addition of electrolyte which may be up to 10% (w/v), preferably up to 2%, and most preferably <1%.

(9) Extent of mixing of the components. This issue mainly relates to degree of stirring and preferably stirring is achieved such that the starting solutions (i.e. M, L and buffer) are rapidly mixed and maintained homogenous throughout.

It will be apparent to those skilled in the art that while the above variables may all control the physico-chemical nature of the precipitate, further variables such as the collection system and/or excipients used for the recovery of the precipitate, which may involve purposeful inhibition of agglomeration, its drying and its grinding may subsequently affect the material properties. However, these are general variables to any such system for solid extraction from a solution phase. After separation of the precipitated material, it may optionally be dried before use of further formulation. The dried product may, however, retain some water and be in the form of a hydrated solid phase ligand-modified poly oxo-hydroxy metal ion material. It will be apparent to those skilled in the art that at any of the stages described herein for recovery of the solid phase, excipients may be added that mix with the ligand-modified poly oxo-hydroxy metal ion material but do not modify the primary particle and are used with a view to optimising formulation for the intended function of the material. Examples of these could be, but are not limited to, glycolipids, phospholipids (e.g. phosphatidyl choline), sugars and polysaccharides, sugar alcohols (e.g. glycerol), polymers (e.g. polyethyleneglycol (PEG)) and taurocholic acid.

Formulations and Uses

The solid phase materials of the present invention may be formulated for use in a range of biologically relevant applications, including formulation for use as pharmaceutical, nutritional, cosmetic, or personal hygiene compositions. The compositions of the present invention may comprise, in addition to one or more of the solid phase materials of the invention, a pharmaceutically acceptable excipient, carrier, buffer, stabiliser or other materials well known to those skilled in the art. Such materials should be non-toxic and should not interfere with the efficacy of the solid phase materials for the application in question.

The precise nature of the carrier or other component may be related to the manner or route of administration of the composition. These compositions may be delivered by a range of delivery routes including, but not limited to: gastrointestinal delivery, including orally and per rectum; parenteral delivery, including injection; dermal delivery including patches, creams etc; mucosal delivery, including nasal, inhalation and via pessary; or by implant at specific sites, including prosthetics that may be used for this purpose or mainly for another purpose but have this benefit.

Pharmaceutical compositions for oral administration may be in a tablet, capsule, powder, gel or liquid form. A tablet may include a solid carrier such as gelatin or an adjuvant. Capsules may have specialised properties such as an enteric coating. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Where the solid ligand-modified poly oxo-hydroxy metal ion material needs to be maintained in a solid form, e.g. to control the delivery of a component of the material, it may be necessary to select components of the formulation accordingly, e.g. where a liquid formulation of the material is made.

For intravenous, cutaneous or subcutaneous injection, or injection at the site of affliction, the active ingredient will be in the form of a parenterally acceptable aqueous solution or suspension which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The materials and compositions used in accordance with the present invention that are to be given to an individual are preferably administered in a "prophylactically effective amount" or a "therapeutically effective amount" (as the case may be, although prophylaxis may be considered therapy), this being sufficient to show benefit to the individual (e.g. bioavailability). The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

Examples of the uses of the solid ligand-modified poly oxo-hydroxy metal ion materials disclosed herein include, but are not limited to, uses as: dietary mineral supplements and fortificants; therapeutic mineral supplements (e.g. as administered by i.v. and oral routes); drugs, nutrients or cosmetic carriers/co-complexes; phosphate binding agents; other binding or sequestering applications; food additives; anti-perspirants; sun-protection agents; vaccine adjuvants; immuno-modulatory agents; direct cosmetic applications including exfoliating agents; bone and dental filler/cements; implant materials including brachytherapy, and imaging and contrast agents.

Ligand-modified poly oxo-hydroxide materials may be used as supplements for nutritional or medical benefit. In this area, there are three main examples:
(i) Therapeutic (prescription) supplements, which are generally administered by the oral or i.v. routes for the treatment of indications including iron deficiency anaemia, iron deficiency and anaemia of chronic disease. The therapeutic administration of materials of the present invention may be in conjunction with other therapies and especially with the concomitant use of erythropoietin.
(ii) Nutritional (self prescribed/purchased supplements) which are usually for oral delivery.
(iii) Fortificants. These may be traditional forms—in terms of being added to food prior to purchase—or more recent fortificant forms such as 'Sprinkles' which are added (like salt or pepper) to food at the time of ingestion.

In all formats, but most especially for fortificants, subsequent formulation, such as addition of a protective coating (e.g. lipid), may be necessary to make the material compatible with its intended usage. In addition, any of these supplemental forms can be co-formulated, either by incorporation within the material through use of co-formulated material(s) as ligand(s) or through trapping/encapsulation of said materials, or simply through co-delivery of said materials.

As described herein, one particular application of the solid ligand-modified poly oxo-hydroxy metal ion materials of the present invention is for the treatment of mineral deficiencies, for example iron deficiency. In an alternative application the materials may be employed to bind or sequester a component present in an individual. By way of example, the ferric iron compositions disclosed herein may be used to deliver iron to an individual for use in the prophylaxis or treatment of iron deficiency or iron deficiency anaemia which may be suspected, or diagnosed through standard haematological and clinical chemistry techniques. Iron deficiency and iron deficiency anaemia may occur in isolation, for example due to inadequate nutrition or due to excessive iron losses, or they may be associated with stresses such as pregnancy or lactation, or they may be associated with diseases such as inflammatory disorders, cancers and renal insufficiency. In addition, there is evidence that the reduced erythropoiesis associated with anaemia of chronic disease may be improved or corrected by the effective delivery of systemic iron and that co-delivery of iron with erythropoietin or its analogues may be especially effective in overcoming reduced erythropoietic activity. Thus, by way of further example, the ferric iron compositions disclosed herein may be used to deliver iron to an individual for use in the treatment of sub-optimal erythropoietic activity such as in anaemia of chronic disease. Anaemia of chronic disease may be associated with conditions such as renal insufficiency, cancer and inflammatory disorders. As noted above, iron deficiency may also commonly occur in these disorders so it follows that treatment through iron supplementation may address iron deficiency alone and/or anaemia of chronic disease. It will be recognised by those skilled in the art that the above examples of the medical uses of iron supplements are by no means limiting.

Experimental Description

Introduction

Inorganic mineral-based materials have widespread biological applications that include: dietary supplements, phosphate binding agents, antacids, immune adjuvants (alum) and antiperspirants (alum). These are often co-formulated in such a way that the mineral physico-chemical properties, such as rates of dissolution and/or disaggregation, are modestly altered in an attempt to improve their efficacy. We have however developed a procedure whereby the actual structure, at the level of the primary particle (the primary unit within the lattice structure), can be modified within oxide/hydroxide minerals. This nano-structuring can lead to profound changes in mineral characteristics and can be tuned to provide mineral with precisely specified physico-chemical characteristics. Moreover the methodology is cheap and can be applied on as large a scale as required. The modifying agents are all biologically compatible, food grade ligands allowing rapid introduction of novel materials to human subjects. An exemplar of these materials is the production of a novel class of iron supplements that may have therapeutic parenteral and oral applications, as well as widespread roles as fortificants and dietary supplements.

With supplements, we believe that one desirable property is that the rate of nutrient absorption mimics that seen for the same nutrient when ingested in a food. For example, with iron, the rate of dietary iron absorption can be controlled through the rate of iron dissolution. In the following examples, we have produced a number of different solid ligand-modified poly oxo-hydroxy metal ion materials using the process of the present invention, with the aim of identifying compositions that release iron in a controlled fashion. The aim is that the rate of dissolution will allow the ferric iron to be donated to the mucosal reductase (DcytB) in a fashion that prevents build up of iron in the lumen or bolus absorption into the circulation—neither of which are desirable. Thus the ferric iron compositions of the present invention should have lower gastrointestinal side effects as they will not undergo facile redox cycling in the gut. In addition, there is scope to design the compositions to dissolve differently at gastric pH versus intestinal pH. There is also the possibility of tailoring the compositions to dissolve at different rates depending upon the concentration of iron in the local solution (e.g. the gut lumen), such that the compositions may 'sense' iron requirements of the environment and thus iron requirements of the individual. The remaining, unabsorbed luminal iron would be largely unavailable for undesirable redox reactivity within the lumen and would pass harmlessly into the faeces.

Nomenclature of Materials

Throughout the examples the $FeOHL_A$-i:j-$L_B$k nomenclature was adopted to describe the preparation for ligand-modified poly oxo-hydroxy ferric iron materials; where $L_A$ refers to the ligand with higher solution affinity and $L_B$ to the ligand with lower solution affinity for iron. The ratio i:j refers to the molar ratio between iron (Fe) and ligand A ($L_A$) and k refers to the concentration (mM) of ligand B ($L_B$) in solution prior to the precipitation of ligand-modified poly oxo-hydroxy ferric materials. Where only a weaker ligand (ligand B) was present the nomenclature used was FeOH $L_B$k. For example, the material defined as FeOHT-3:1-Ad20 was prepared using a molar ratio of three Fe to one tartrate and a concentration of adipate of 20 mM. The iron concentration in solution was 40 mM unless stated otherwise in the figure legends.

Materials

All chemicals were purchased from Sigma-Aldrich, Dorset, UK, unless otherwise specified. All laboratory ware was in polypropylene. The materials used in the preparation of the ligand-modified poly oxo-hydroxy ferric iron materials for the in vivo study were prepared with food grade chemicals or pharmaceutical grade chemicals also from Sigma-Aldrich, with the exception of the $^{58}Fe$ elemental iron used in the preparation of the $^{58}Fe$ ferric chloride which was purchased from Chemgas, Boulogne, France.

Methods

Screening Assay

A series of dietary ligands was tested in a screening assay for their effects on the formation of solid ligand-modified poly oxo-hydroxy metal ion materials. Briefly, in a centrifuge tube, a fixed volume of stock solution of ferric iron (400 mM $FeCl_3$ with 50 mM MOPS, pH 1.4) was mixed with varying volumes of a stock solution of ligand (400 mM with the exception of maltol which was 200 mM, plus MOPS at 50 mM and 0.9% NaCl) to obtain the desired metal:ligand ratio. The volumes were then equally adjusted to parity with a solution of 50 mM MOPS and 0.9% NaCl. All the solutions obtained at this stage were fully soluble at pH<2.0. A small aliquot was taken to confirm the starting iron concentration and then the pH was raised to ~6.5 by drop-wise addition of concentrated NaOH to avoid high volume changes. After centrifugation at 2500 rpm for 10 minutes, an aliquot of supernatant was taken to analyse the iron remaining in solution. The remaining supernatant was discarded and a fixed volume of dissolution buffer at pH 6 (MOPS10 mM) or pH 4 (Acetic acid 10 mM) was then added to the wet solid of each tube and incubated overnight at room temperature. The tubes were then centrifuged (2500 rpm for 10 minutes) and an aliquot of supernatant taken to determine the iron that was disaggregated. The iron concentration in each aliquot was measured by ICPOES analysis.

Titration Experiments

An acidic concentrated stock solution of iron (as ferric chloride) was added to a solution containing either the ligand A, ligand B or both ligand A and B at appropriate concentrations to obtain the desired M:L ratios. In some cases 0.9% w/v of electrolyte (for example NaCl or KCl) was also added. The solution was mixed thoroughly and an aliquot collected for analysis of the "starting iron" concentration. The pH of the solution was always <2.0 and the iron fully solubilised. Next the pH was slowly increased by drop-wise addition of a concentrated solution of NaOH with constant agitation until the mixture reached a basic pH (generally >8.0). At different points during the titration, a homogeneous aliquot (1 mL) of the mixture was collected and transferred to an Eppendorf tube. Any aggregate formed was separated from the solution by centrifugation (10 minutes at 13000 rpm). The iron concentration in the supernatant was assessed by ICPOES. In some cases the supernatant was analysed for the presence of aquated particulate iron and the size distribution was measured (see below). When aquated particulate iron was present, the supernatant was ultrafiltrated (Vivaspin 3,000 Da molecular weight cut-off polyethersulfone membrane, Sartorius Stedium Biotech GmbH, Goettingen, Germany) and the iron concentration in the filtrate, i.e. "soluble iron", was analysed by ICPOES.

Preparation of Solid Ligand-Modified Poly Oxo-Hydroxy Ferric Iron Materials

The materials were prepared following a protocol similar to the titration experiment described above. Briefly, an acidic concentrated stock solution of iron was added to a solution containing either the ligand A, ligand B or both ligand A and B. In some cases 0.9% w/v of electrolyte was also added. The "starting pH" of the solution was always <2.0, and the iron fully solubilised. The pH was then slowly increased by drop-wise addition of a concentrated solution of NaOH with constant agitation until reaching the desired final pH.

When preparing the solid material as a pellet, the entire mixture was then transferred to a centrifuge bottle and spun at 4500 rpm for 15 minutes. The supernatant was discarded and the aggregated solid phase collected in a petri dish. When necessary, the solid was then dried in an oven at 45° C. for a minimum of 8 hours. Alternatively, the mixture (precipitate and supernatant) was freeze-dried at −20° C. and 0.4 mbar.

When preparing the solid material as aquated particulate material, the total mixture was either freeze-dried as above, or concentrated by ultrafiltration (Vivaspin 3000 Da molecular weight cut-off polyethersulfone membrane, Sartorius Stedium Biotech GmbH, Goettingen, Germany) and then air dried in an oven at 45° C. for a minimum of 8 hours. In some cases the mixture was dialysed (1,000 Da regenerated cellulose membrane Spectra/pro 7, Cole-Parmer, London, UK) in water to remove excess iron, ligands and electrolytes before undergoing one of the drying processes described above.

When using bicarbonate as ligand B a variation of this protocol was used to avoid release of $CO_2$ from transformation of bicarbonate at acidic pH. The starting solution containing ligand A (when applicable) and bicarbonate was prepared at pH 8.5. The appropriate volume of acidic concentrated stock solution of iron was then added drop-wise in conjunction with NaOH pellets (progressively added to the mixture as required) in order to always maintain a pH>7.5. The final pH of the preparation was 8.5.

Disaggregation Assay

Known amounts of solid ligand-modified poly oxo-hydroxy ferric iron materials were added into tubes (about 3 mg iron per tube). Then, 3 mL of buffer (see below) were added and the tubes shaken vigorously and incubated at room temperature overnight. After centrifugation at 4500 rpm for 15 minutes to separate the aggregated solid phase from the aquated phase, an aliquot of supernatant was collected to measure the disaggregated iron concentration. The remaining supernatant was discarded. The mass of remaining material (i.e. the wet pellet) was recorded. Concentrated $HNO_3$ was added to this pellet and the new mass recorded. The tubes were left at room temperature until all the pellet dissolved and an aliquot was collected for ICPOES analysis to determine the iron concentration in the wet pellet.

The buffers were either 50 mM MOPS with 0.9% NaCl at pH 7.0; 50 mM Maleic acid with 0.9% NaCl at pH 5.8-6.0 and 1.8-2.2; 50 mM sodium acetate/50 mM acetic acid glacial with 0.9% NaCl at pH 4.0-4.5.

In Vitro Gastrointestinal Digestion Assay

An amount of the solid ligand-modified poly oxo-hydroxy ferric iron materials or control iron materials namely ferrous sulphate, ferric chloride, or unmodified ferric oxo-hydroxide, equivalent to 60 mg elemental iron, were added to a synthetic gastric (stomach) solution (50 mL of 2 g/L NaCl, 0.15 M HCl and 0.3 mg/mL porcine pepsin) and incubated at 37° C. for 30 minutes with radial shaking. Then 5 mL of the resulting gastric mixture was added to 30 mL of synthetic duodenal solution (containing 10 g/L pancreatin and 2 g/L NaCl in 50 mM bicarbonate buffer pH 9.5). The final volume was 35 mL and the final pH was 7.0. The mixture was incubated at 37° C. for 60 min with radial shaking. Homogeneous Aliquots (1 mL) were collected at different time points during the process and centrifuged at 13,000 rpm for 10 minutes to separate the aggregate and aquated phases. The supernatant was analysed for iron content by ICPOES. At the end of the experiment, the remaining solution was centrifuged at 4,500 rpm for 15 min and the supernatant analysed for Fe content by ICPOES. The mass of remaining material (i.e. the wet pellet) was recorded. Concentrated $HNO_3$ was added to this wet pellet and the new mass recorded. The tubes were left at room temperature until all the pellet dissolved and an aliquot was collected for ICPOES analysis to determine the quantity of iron that did not disaggregate/dissolve. The starting amount of iron was calculated from the iron in the wet pellet plus the iron in the supernatant.

To differentiate between soluble iron and aquated particulate iron in the supernatant, at each time point, this fraction was also ultrafiltered (Vivaspin 3,000 Da molecular weight cut-off polyethersulfone membrane, Sartorius Stedium Biotech GmbH, Goettingen, Germany) and again analysed by ICPOES.

The gastrointestinal digestion of commercial iron preparations was also tested with this assay using the dose of total iron recommended by the manufacturers: Ferric pyrophosphate 14 mg (Lipofer, Boots); ferrous bisglycinate 20 mg (Gentle iron, Solgar); ferric-hydroxide polymaltose complex 80 mg (Maltofer, Ferrum Hausmann); ferric tri-maltol 30 mg (Trimaltol, Iron Unlimited).

Modified In Vitro Gastrointestinal Digestion Assay

The particle size of the ligand-modified poly oxo-hydroxy ferric iron materials under simulated gastric and intestinal conditions was determined using an adapted "in vitro gastrointestinal digestion assay" in which no protein was in solution. The absence of proteins was required to measure particle size as these interfere with the measurement but the procedure was otherwise identical to the "in vitro gastrointestinal digestion assay" with extra aliquots being collected at various time points for the determination of particle size.

Inductively Coupled Plasma Optical Emission Spectroscopy Analysis (ICPOES)

Iron contents of solutions or solids (including wet solids) were measured using a JY2000-2 ICPOES (Horiba Jobin Yvon Ltd., Stanmore, U.K.) at the iron specific wavelength of 259.940 nm. Solutions were diluted in 5% nitric acid prior to analysis while solids were digested with concentrated $HNO_3$. The percentage of iron in solution or solid phase was determined by the difference between the starting iron content and either the iron in the soluble phase or the iron in the solid phase depending on the assay.

Determination of Particle Size

The size distribution of micron-sized particles was determined using a Mastersizer 2000 with a Hydro-µP dispersion unit (Malvern Instruments Ltd, Malvern, UK) and nano-sized particles were determined with a Zetasizer Nano ZS (Malvern Instruments Ltd, Malvern, UK). Mastersizer measurements required no sample pre-treatment whereas centrifugation was needed to remove large particles prior to Zetasizer measurements.

Structural Analysis

Transmission Electron Microscopy and Energy Dispersive X-Ray Analysis (EDX)

Powder samples were analysed by first dispersing the powder in methanol and then drop-casting on standard holey carbon TEM support films. Commercial tablets were similarly analysed but were first crushed to release the powder. Analysis were undertaken by the Institute for Materials Research, University of Leeds, UK.

Scanning Transmission Electron Microscopy

Powder samples were analysed by first dispersing the powder in methanol and then drop-casting on standard holey carbon TEM support films. Commercial tablets were similarly analysed but were first crushed to release the powder. Analysis were undertaken by aberration-corrected scanning transmission electron microscopy (Daresbury; superSTEM).

Infrared Analysis (IR)

IR spectra were collected using a DurasamplIR diamond ATR accessory with a Nicolet Avatar 360 spectrometer with a wavelength range of 4000-650 $cm^{-1}$ and resolution of 4 $cm^{-1}$. Analysis were undertaken by ITS Testing Services (UK) Ltd, Sunbury on Thames, UK.

X-Ray Diffraction Analysis

Samples were analysed as dry powders. Commercial tablets were crushed to release the powder. Analysis was by X-ray diffraction analysis at the University of Cambridge using a Philips X'Pert PW3020 (theta/2theta, 2 motors) with up to 14 hour scan time and 5-70° 2theta on CuKalpha.

In Vivo Absorption Study

Subjects

Healthy young women (aged 18-45 years) with mild iron deficiency anaemia (defined as haemoglobin between 10-11.9 g/dL plus either serum ferritin below 20 µg/L or transferrin saturation below 10%); or clear iron deficiency (defined as serum ferritin below 12 µg/L) were recruited to take part in the study. Exclusion criteria were pregnancy or lactation and known coeliac disease, moderate/severe anaemia (haemoglobin levels <10 g/dL), cardiovascular disease, chronic respiratory disease, chronic liver disease, renal disease, chronic infection, or chronic inflammation. Other exclusion criteria were: surgery in the past three months, cancer diagnosis in the last ten years, known history of hereditary haemochromatosis or haemoglobinopathies, current medication that could alter iron metabolism, recent blood donation/heavy blood loss (in the past 3 months). Subjects who regularly consume vitamin and mineral supplements were asked to discontinue supplementation 2 weeks before the screening for the study. Written informed consent was obtained from all subjects. The study protocol was approved by the Suffolk Local Research Ethics Committee.

Study Design

The experimental treatment was either a single dose of $^{58}Fe$ labeled ligand-modified poly oxo-hydroxy ferric iron material (60 mg total iron) or ferrous sulphate (65 mg total iron). Ferrous sulphate is used as a reference dose to control for individuals who are poor absorbers (defined as those who have no significant net area under the curve (AUC) for plasma iron following ferrous sulphate ingestion). A crossover study design was used with each volunteer acting as her own control.

Fe absorption was based on erythrocyte incorporation of the $^{58}$Fe stable-isotope label 14 days after the intake of labelled iron test compounds. The test compounds and the reference compound (ferrous sulphate) were taken (with or without breakfast), under strictly standardised conditions and close supervision, after an overnight fast with 14 days interval. No intake of food or fluids (apart from water) was allowed for 4 h after the iron compound intake.

Ten blood samples (12 mL) were taken during each of the 2 visits to determine the absorption of Fe at the following times: before intake and 30, 60, 90, 120, 180, 210 and 240 minutes after intake of the iron compound. An additional blood sample was taken at baseline (before intake) to confirm iron status (full blood count, ferritin, soluble transferrin receptor, transferrin saturation) and determine erythrocyte $^{58}$Fe incorporation.

Total serum iron concentration was analysed by a standard clinical chemistry procedure based on the method by Smith et al using the chromophore Ferene®.

RBC incorporation of $^{58}$Fe was determined using an Elan DRC Plus Inductively Coupled Plasma Mass Spectrometer (Perkin Elmer Sciex, Beaconsfield, UK). The sample introduction system consisted of a V-groove nebuliser, a double-pass spray chamber, a demountable quartz torch, and a quartz injector (2 mm internal diameter). Platinum-tipped sampler and skimmer cones (Perkin Elmer Sciex, Beaconsfield, UK) were used for all analyses. Baseline whole blood samples were collected from participants in the study immediately prior to administration of a 60 mg oral Fe supplement labelled with 2 mg $^{58}$Fe, and a second blood sample was collected 14 days after administration. Whole blood was diluted 100-fold with an aqueous solution containing 0.5% Triton X-100, 1% butan-1-ol, 0.5% ammonia, and 0.007% nitric acid. Instrument conditions were tuned for optimum signal sensitivity (via the measurement of $^{24}$Mg, $^{115}$In and $^{238}$U isotopes), minimum oxide formation (via the measurement of the $^{140}$Ce and $^{155}$Gd isotopes to allow monitoring of the degree of CeO formation at m/z=155) and minimum doubly charged ion formation (via the measurement of the $^{138}$Ba and $^{69}$Ga isotope signals to allow monitoring of the degree of $^{138}$Ba$^{2+}$ formation at m/z=69). Further adjustment was then performed to reduce mass bias between $^{58}$Fe and $^{57}$Fe (approximately 5%). Detector voltages were dropped from the typical −2400 and 1550 V to −1725 and 1050 V for analogue and pulse stages, respectively.

Preparation of $^{58}$Fe Labelled Ferric Chloride Solution

A solution of $^{58}$Fe labelled ferric chloride was prepared by dissolving 100 mg $^{58}$Fe enriched elemental iron (Chemgas, Boulogne, France) in 4 mL 37% HCl in a pear-shaped glass flask attached to a condenser and heated at 48° C. in a water bath. The temperature was raised gradually over time to keep the solution boiling as the concentration of chlorine dropped. When the elemental iron powder was dissolved, 0.5 mL of 30% hydrogen peroxide were added to oxidize ferrous iron to ferric iron. The flask was then sealed, once the oxidation reaction finished, i.e. once the formation of $O_2$ bubbles stopped. The concentration of iron in the final solution was determined by ICPOES and the Ferrozine assay was used to confirm the absence of ferrous iron.

Preparation of the $^{58}$Fe Labelled Ligand Modified Poly Oxo-Hydroxy Ferric Iron Material The chosen ligand-modified poly oxo-hydroxy ferric iron materials enriched with $^{58}$Fe were prepared following the protocol described above (see Preparation of solid ligand-modified poly oxo-hydroxy ferric iron materials) using a ferric chloride stock solution containing 3.5% w/w $^{58}$Fe (2 mg of $^{58}$Fe per 60 mg total iron in the ingested solid material) from the $^{58}$Fe labelled ferric chloride solution discussed above.

Results and Discussion

Effect of Ligand A

A series of ligands, namely maltol, succinic acid, citric acid, lactic acid, tartaric acid, malic acid, gluconic acid, aspartic acid, glutamic acid, histidine and glutamine, were studied for their effect on ferric poly oxo-hydroxide precipitation from solution.

Initially, the ligands were all tested using the screening assay described above at ratios of 1:1 to 1:5 and classified in three groups. The first group, "strong ligands", were ligands found to inhibit the formation of 80% of the solid material at ratio 1:1 and included gluconic acid, citric acid and maltol. The second group, "weak ligands", were ligands found to have little effect on the amount of solid material formed (<10% at all the ratios tested) and included aspartic acid, succinic acid, lactic acid, glutamic acid and histidine. The third group, "intermediate ligands", were ligands found to have an influence, between strong and weak ligands, on the amount of solid material formed at, at least, one of the ratios tested and included malic acid, tartaric acid and glutamine.

In a second instance, six ligands from the three groups described above were re-screened for their effects on both the formation of ferric poly oxo-hydroxide precipitation at varying M:L ratios, and the dissolution of the solid materials formed in pH 6 and pH 4 buffers (see screening assay above). As expected, the ligands had variable effects on the percentage of poly oxo-hydroxy iron that was precipitated depending upon (a) the group the ligand belonged to and (b) the M:L ratio. Yet, the solid materials formed, showed variable re-aquation properties that were not predictable from the precipitation behaviours. Examples of results using a strong affinity ligand, namely maltol, a weak affinity ligand, namely succinate, and an intermediate affinity ligand, namely malate, are shown in FIGS. 1A and B. Re-dissolution clearly depends upon the ligand and its ratio to iron which may be expected. What is not expected is that the strong ligand, maltol, did not promote any re-dissolution of the iron at pH 6.0 in spite of the fact that soluble iron-maltol complexes can be formed (for at least a proportion of the iron) at this pH. Moreover, the intermediate ligand, malate, allowed greater dissolution of iron from the solid phase at pH 6.0 than the strong ligand maltol—even when ratios were matched (c.f. 1:1). Examples of further results with other ligands or ratios are shown in Table 1.

TABLE 1

The effect of single ligands on poly oxo-hydroxy iron precipitation and the re-dissolution of that iron.

| Ligand | M:L ratio | % Fe precipitated at pH 6.5 | % Fe re-dissolved at pH 6 | % Fe re-dissolved at PH 4 |
| --- | --- | --- | --- | --- |
| Succinic acid | 1:1 | 100 | 0 | 0 |
| L-lactic acid | 1:1 | 65 | 0 | 0 |
| Maltol | 3:1 | 55 | 0 | 13 |
| Tartaric acid | 5:1 | 85 | 36 | 100 |
| Citric acid | 5:1 | 42 | 0 | 0 |

Two ligands, namely malate and tartrate, that showed most effects in the screening assay, were chosen for study in greater detail. The re-dissolution profile was studied using a more defined assay in four different buffers (see Disaggregation Assay in Methods). The buffers contained 0.9% w/v electrolyte so that the results obtained would reflect the behaviour of the material in a biological ionic strength environment. Also the pH environments were chosen to reflect different parts of the gastrointestinal tract from gastric (pH 1.8) to intestinal (pH 7.0). Firstly, the results shown in Table 2 confirmed that the two ligands affected not only the precipitation but also the disaggregation profile depending on the ratio used in the preparation of the ferric poly oxo-hydroxide materials as seen in the screening assay above. Generally, increasing the ligand ratio decreased the formation of the ligand-modified poly oxo-hydroxy ferric iron solid material and increased the disaggregation profile. However, the extent of the effect seen with one ligand did not reflect the extent of the effect seen with another ligand as illustrated here with malate and tartrate. The results observed were reproducible as indicated in table 2 with malate at M:L ratio 1:2.

TABLE 2

Effect of malate and tartrate ratios on the percentage of iron precipitated as ligand-modified poly oxo-hydroxy ferric iron materials and the disaggregation of the materials.

| Ligand | M:L ratio | % Fe precipitated | % Fe disaggregated at pH | | | |
|---|---|---|---|---|---|---|
| | | | 7.0 | 5.8 | 4.1 | 1.8 |
| Malic acid[a] | 2:1 | 59 | 6 | 7 | 19 | 14 |
| | 1:1 | 45 | 12 | 20 | 55 | 15 |
| | 1:2 (n = 4) | 27 ± 10 | 6 ± 4 | 49 ± 5 | 63 ± 5 | 18 ± 4 |
| Tartaric acid[b] | 4:1 | 99 | 13 | 61 | 99 | 22 |
| | 3:1 | 91 | 71 | 100 | 100 | 28 |
| | 2:1 | 43 | 100 | 100 | 100 | 14 |

Ligand-modified poly oxo-hydroxy ferric iron materials were prepared at pH 6.5 in 50 mM MOPS and 0.9% NaCl.

Starting iron concentrations were 26.7 mM. Precipitation steps were either carried out in individual tubes (a) as per the precipitation procedure described in Screening Assay, or as a batch (b) as per the preparation of solid ligand-modified poly oxo-hydroxy ferric iron materials (see methods). Disaggregation of all materials was performed according to the method outline in Dissagregation assay (see methods).

Figure 2:
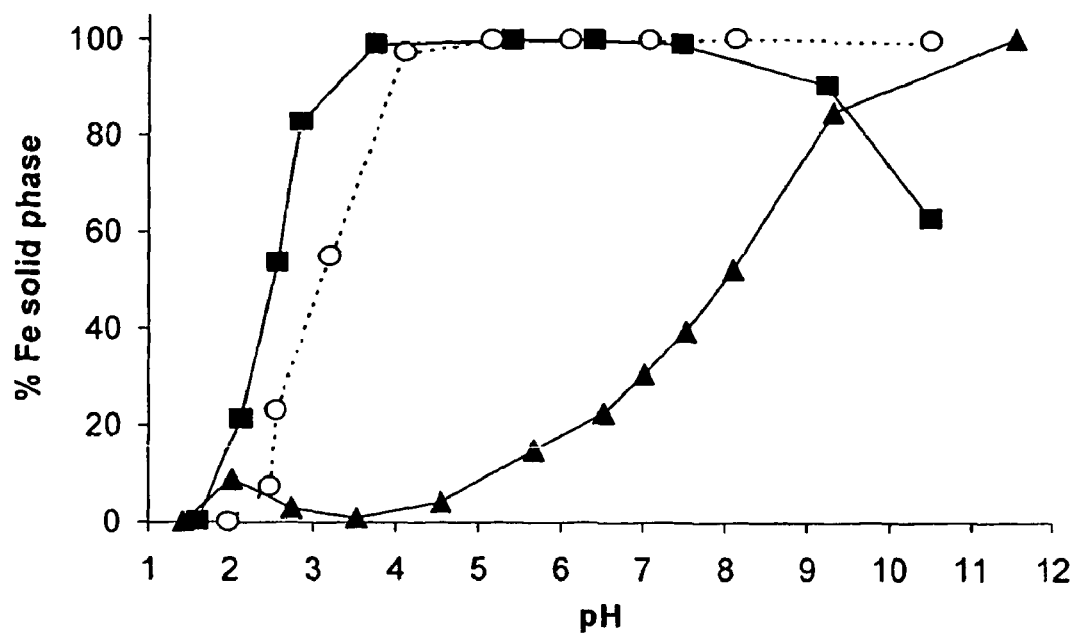
FIG. 2: Effect of different ligands on the evolution of precipitation of solid ligand-modified poly oxo-hydroxy metal ion materials with increasing pH as described in titration protocol: no ligand (open circle), tartaric acid (closed square) and malic acid (closed triangle). All were prepared in 50 mM MOPS and 0.9% w/v NaCl. The iron concentration in the initial solution (prior to precipitation) was 27 mM.
Figure 16:
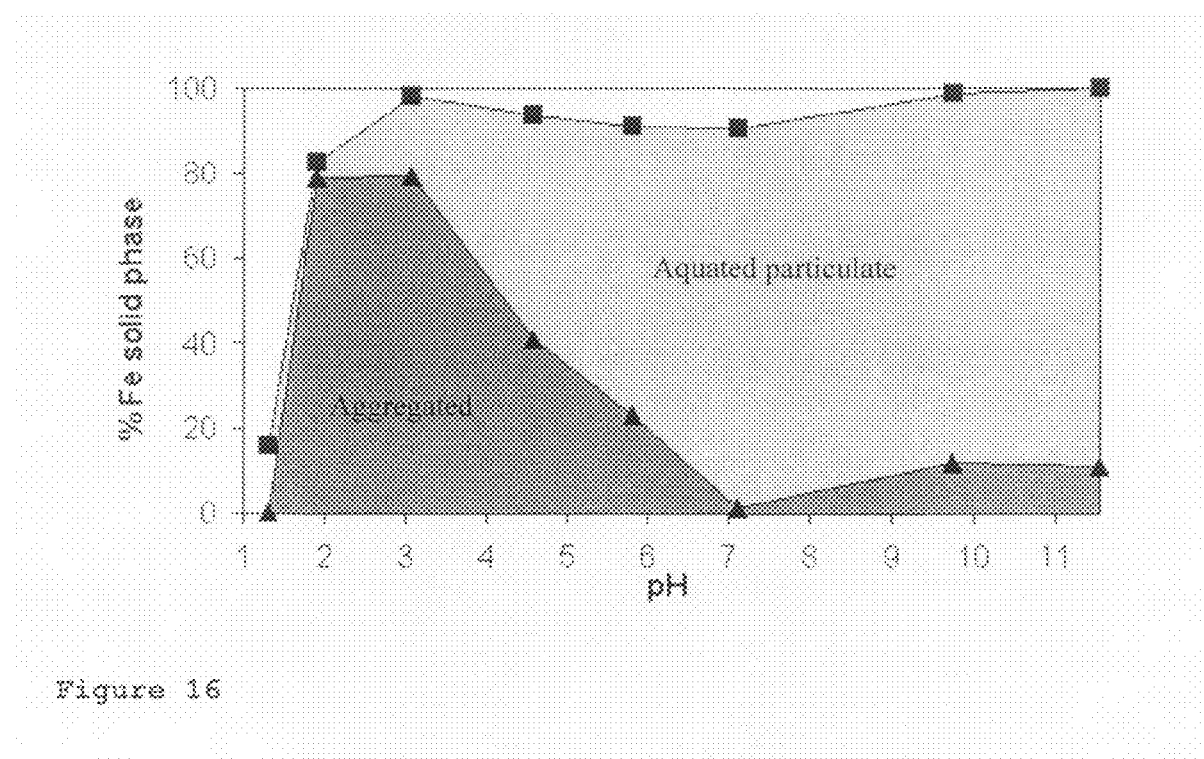
FIG. 16: Evolution of the formation of the ligand-modified poly oxo-hydroxy ferric materials, namely FeOHT-2:1-Ad20, with increasing pH, as described in the titration protocol in Methods, and expressed as the percentage of total iron in the starting solution. Percentage iron in the aggregated material is shown by the closed triangles while the percentage of iron in both the aggregated and aquated particulate materials is shown by the closed square. Note: the remaining iron (i.e. the iron that is not in the aggregated or aquated particulate form) is in the soluble phase.

Secondly, the effect of the ligand on the rate of formation of the ligand-modified poly oxo-hydroxy ferric iron materials was studied using the titration protocol described in the methods section. FIG. 2 shows the rate of formation of the solid material with increasing pH. The addition of malate was found to delay the formation of the solid material compared to the absence of ligand. This scenario is to be expected when a ligand competes with the polymerisation of the poly oxo-hydroxy ferric iron entity that results in the formation of the solid material. However, unexpectedly, tartrate was found to have a promoting effect on the formation of the solid material at lower pH. This does not correlate with the competition scenario described above. In this case the ligand, tartrate, appears to be enhancing the precipitation. Another observation was that tartrate, at basic pH (>7.5), did promote disaggregation of this material. Indeed, FIG. 16 shows a typical profile of the formation of two solid phases, namely aggregated and aquated tartrate-modified ferric poly oxo-hydroxide with increasing pHs following the titration protocol described in Methods. These results were also observed with other ligands A and ligands B (results not shown).

Figure 3:
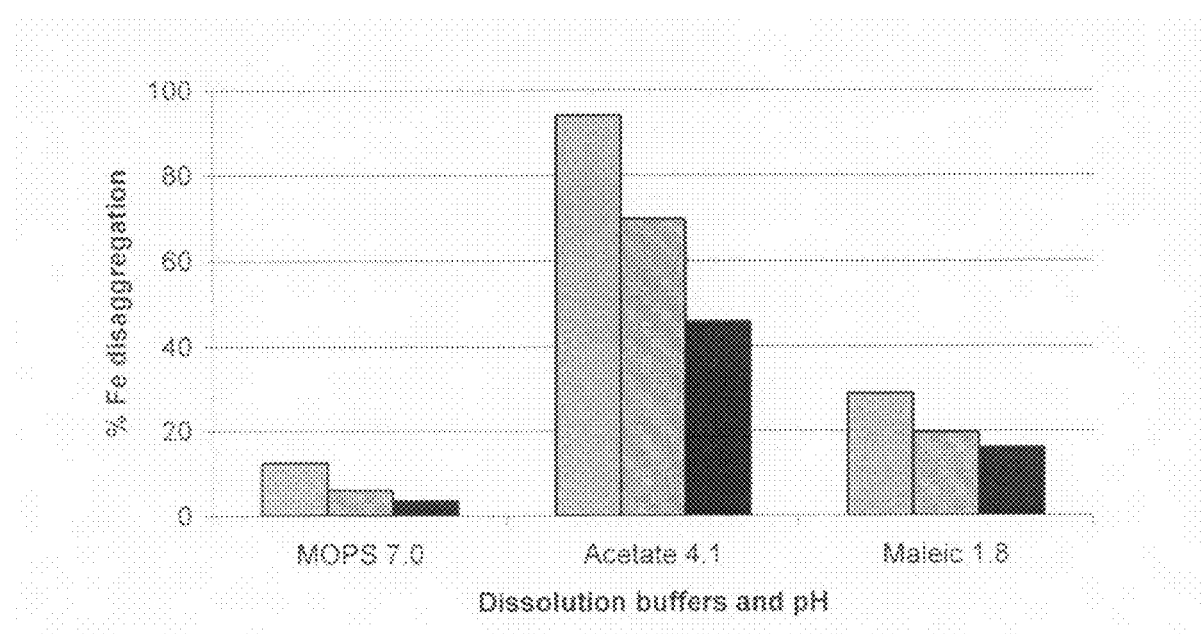
FIG. 3: Example of the effect of varying the pH of the final solution during the preparation of the solid ligand-modified poly oxo-hydroxy metal ion materials on the disaggregation of these wet materials at different pHs in the buffers indicated. The materials, namely FeOHM-1:2-MOPS50, were prepared following the preparation protocol described in Methods with 0.9% w/v NaCl and final pH 6 (grey bars), pH 7 (striped bars) or pH 8 (black bars). The percentage precipitation obtained was 10%, 30% and 48% respectively. The iron concentration in the initial solution (prior to precipitation) was 27 mM.

The disaggregation profile of the ligand-modified poly oxo-hydroxy ferric iron solid material formed at different pHs was shown to vary as illustrated in FIG. 3 for malate. As the pH of preparation of the material increases, the disaggregation profile decreases. This is in accordance with an increase of polymerisation and formation of oxo-bridges with increasing pH, probably limiting the modification effect of the ligand on the material.

Figure 4:
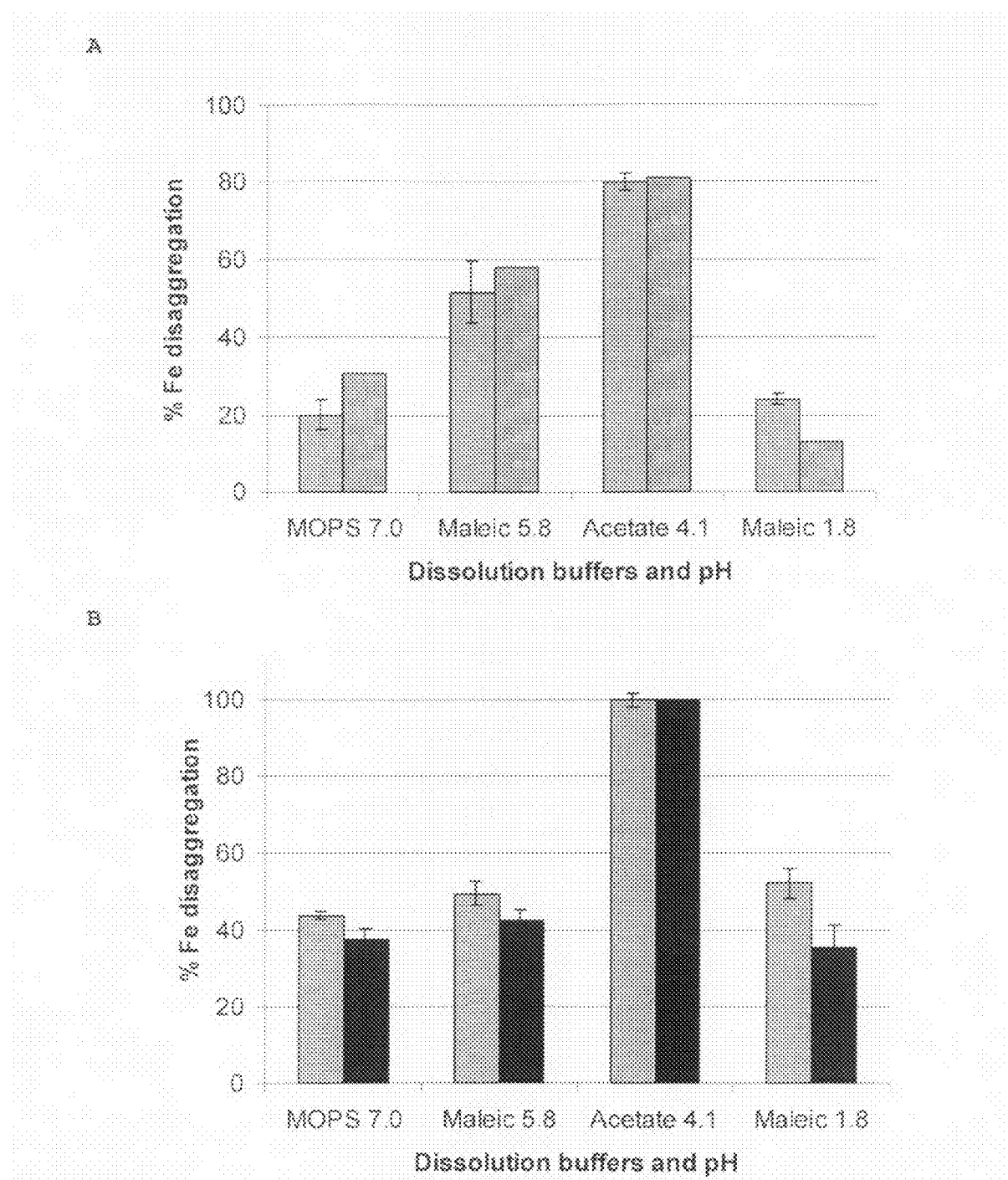
FIG. 4: Example of how the presence of an electrolyte in the preparation of the solid ligand-modified poly oxo-hydroxy metal ion materials can affect the disaggregation of the material at four different pHs in the buffers indicated. Materials were prepared following the preparation protocol described in Methods and oven dried. The materials, namely FeOHT-4:1-MOPS50, were prepared at a final solution pH of 6.5 and formed in the absence of electrolyte (grey bars, n=2) or in the presence of 0.9% w/v NaCl (stripped bars, n=1); the percentage precipitation obtained was 97% and 98% respectively (A). The material, namely FeOHT-2:1-Niacin50, were prepared at a final solution pH of 3.2 in the absence of electrolyte (grey bars, n=2) or in the presence of 0.9% w/v KCl (black bars, n=2); the percentage precipitation obtained was 88% and 91% respectively (B). The iron concentration in the initial solution (prior to precipitation) was 27 mM.

The presence of 0.9% w/v electrolyte, as sodium (NaCl) or potassium chloride (KCl), in the preparation of the ligand-modified poly oxo-hydroxy ferric iron solid materials was also studied. FIG. 4A shows that the presence of 0.9% NaCl did not affect the disaggregation profile of the tartrate-modified poly oxo-hydroxy ferric iron material at M:L ratio 4:1 compared to the same material prepared without NaCl. Similarly, FIG. 4B shows that the presence of 0.9% KCl did change the disaggregation profile of the tartrate-modified poly oxo-hydroxy ferric iron material at M:L ratio 2:1 (solution containing 50 mM niacin).

Figure 5:
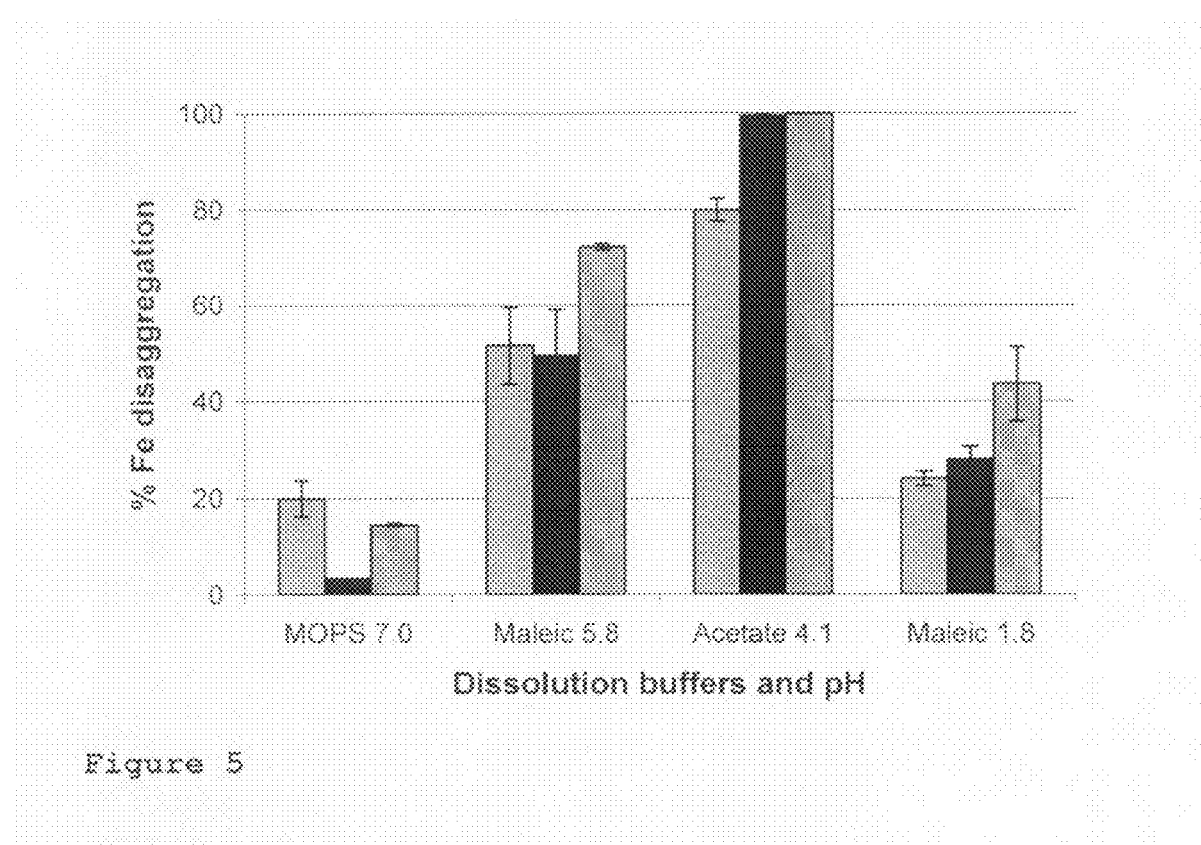
FIG. 5: Example of how drying the solid ligand-modified poly oxo-hydroxy metal ion materials can affect its disaggregation at four different pHs in the buffers indicated. The materials, namely FeOHT-4:1-MOPS50, was prepared following the preparation protocol described in method with a final solution pH of 6.5 in the absence of electrolyte. The percentage precipitation obtained was 97%. The solid phase was divided into three aliquots and either oven dried (grey bars, n=2), or freeze-dried (black bars, n=2) or used wet (stripped bars, n=2). Note: some error bars are too small to be viewed. Data shown in grey bars have been shown previously in FIG. 4A. The iron concentration in the initial solution (prior to precipitation) was 27 mM.

Finally, the effect of drying ligand-modified poly oxo-hydroxy ferric iron solid materials was studied with respect to disaggregation. Drying the material generally lead to a modest reduction in its disaggregation as exemplified by the tartrate-modified poly oxo-hydroxy ferric iron material at M:L ratio 4:1 which is illustrated in FIG. 5. Small, inconsistent differences were observed between oven-drying and freeze-drying methods (FIG. 5).

Effect of Ligand B

Almost all of the studies described above were carried out with ligand-modified poly oxo-hydroxy ferric iron solid materials produced in MOPS buffer. MOPS is often used in metal speciation studies due to its very weak interaction with most metal ions and hence it rarely interferes in the formation of metal complexes. However, MOPS has a pKa of 7.2 and so has a buffering capacity around neutral pH. Thus, although MOPS would not interact directly with iron or prevent the formation of the solid material, it may indirectly influence the formation of the solid by controlling the rate of change in environmental pH. In addition, the buffer used in the preparation of the ligand-modified poly oxo-hydroxy ferric iron solid materials should be safe for human consumption which MOPS is not. Therefore, to study the influence of the buffer, or ligand B, on the formation and re-dissolution properties of the ligand-modified poly oxo-hydroxy ferric iron solid materials, we selected a series of compounds with buffering capacity at varying pH ranges; namely, adipate, bicarbonate, acetate, glutarate, dimethyl glutarate, pimelate, succinate, vanillin, tryptophan, benzoate, propionate, borate, niacin and pyridoxine hydrochloride. FIG. 6 illustrates the effect of changing MOPS for adipate on the rate of formation of the tartrate-modified poly oxo-hydroxy ferric iron solid material at M:L ratio 4:1 (FIG. 6(*i*)), as well as its effect on the otherwise un-modified poly oxo-hydroxy ferric iron solid material (FIG. 6(*ii*)). In both cases, adipate had a promoting effect on the rate of formation of the solid material.

Following these observations, the formation and disaggregation profiles of the tartrate-modified oxo-hydroxy ferric iron solid materials were studied using varying M:L ratios. Adipate reduced the disaggregation capacity of the materials formed (Table 3) compared to MOPS (Table 2), except at gastric pH (pH 1.8) which showed low disaggregation capacity with both buffers. In contrast, in the case of malate-modified poly oxo-hydroxy ferric iron materials, bicarbonate had a negative influence on the percentage of precipitation and the disaggregation capacity of the material (Table 2 and 3). These effects fell off with lower concentrations of adipate but not bicarbonate (Table 3, data in bold).

Figure 7:
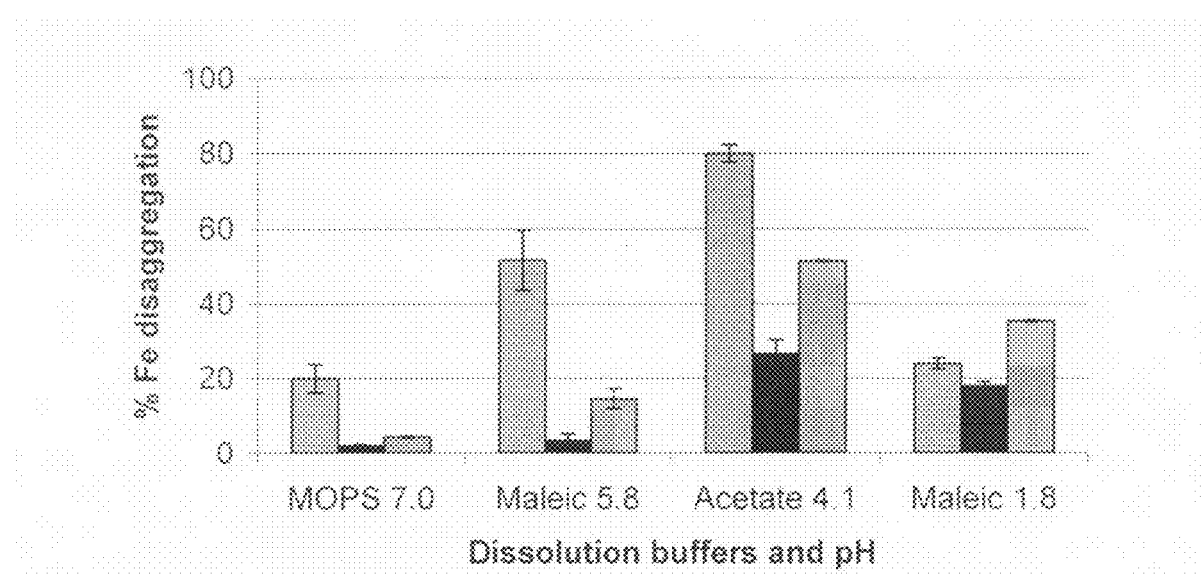
FIG. 7: Example of the effect of ligand B on the disaggregation of oven dried solid ligand-modified poly oxo-hydroxy metal ion materials in four different buffers. Tartrate-modified poly oxo-hydroxy ferric materials at M:$L_A$ ratio 4:1, with tartrate being ligand A ($L_A$), were prepared in the presence of different ligands B being 50 mM MOPS (grey bars, n=2), 20 mM benzoic acid (black bars, n=3) or 50 mM niacin (stripped bars, n=3) following the preparation protocol described in Methods in the absence of electrolyte. The percentage precipitation obtained was 97%, 94% and 100% respectively. Note: some error bars are too small to be viewed. The data indicated in grey bars have been shown previously in FIGS. 4A and 5.

The influence of ligand B on the disaggreagtion profile of the tartrate-modified poly oxo-hydroxy ferric iron solid material is further illustrated in FIG. 7 with niacin and benzoate.

TABLE 3

| Material | M:L ratio | % Fe precipitated | % Fe disaggregated at pH 7.0 | 4.1 | 1.8 |
|---|---|---|---|---|---|
| FeOHT-Ad50 | 2:1 | 41 | 43 | 76 | 17 |
|  | 3:1 | 78 | 13 | 42 | 14 |
|  | 4:1 | 91 | 9 | 50 | 26 |
|  | 5:1 | 96 | 3 | 44 | 27 |
| FeOHT-Ad20 | 3:1 | 82 | 2 | 21 | 17 |
| FeOHM-Bic100 | 1:1 | 5 | nd | nd | nd |
|  | 2:1 | 33 | nd | nd | nd |
|  | 4:1 | 78 | 0 | 1 | 10 |
|  | 5:1 | 81 | 0 | 0.5 | 6 |
| FeOHM-Bic25 | 4:1 | 83 | 0 | 1 | 3 |

Tartrate-modified poly oxo-hydroxy ferric iron solid materials were prepared following the protocol "preparation of solid ligand-modified poly oxo-hydroxy ferric iron materials" (see methods) at pH 4.0 in either 50 mM adipate (Ad50) or 20 mM adipate (Ad20) without the presence of an electrolyte. Malate-modified poly oxo-hydroxy ferric iron solid materials were prepared following the same procedure at pH 8.5 in either 100 mM bicarbonate (Bic100) or 25 mM bicarbonate (Bic25) without the presence of an electrolyte. The disaggregation of the materials was performed according to the method outlined in Disaggregation assay (see method) using the non-dried material for FeOHT-Ad50 and FeOHM-Bic100 and the oven-dried material for FeOHT-Ad20 and FeOHM-Bic25.

Structural Analysis of the Solid Ligand-Modified Poly Oxo-Hydroxy Ferric Iron Materials The solid ligand-modified poly oxo-hydroxy ferric iron materials prepared above differ from currently available iron formulations in that they are not a simple inorganic ferrous ion salt (e.g. ferrous sulphate), an iron complex in which the metal is coordinated with organic ligand (e.g. ferric trimaltol), nor an organic ligand coated iron mineral particle (e.g. iron polymaltose or 'Maltofer').

Figure 11:
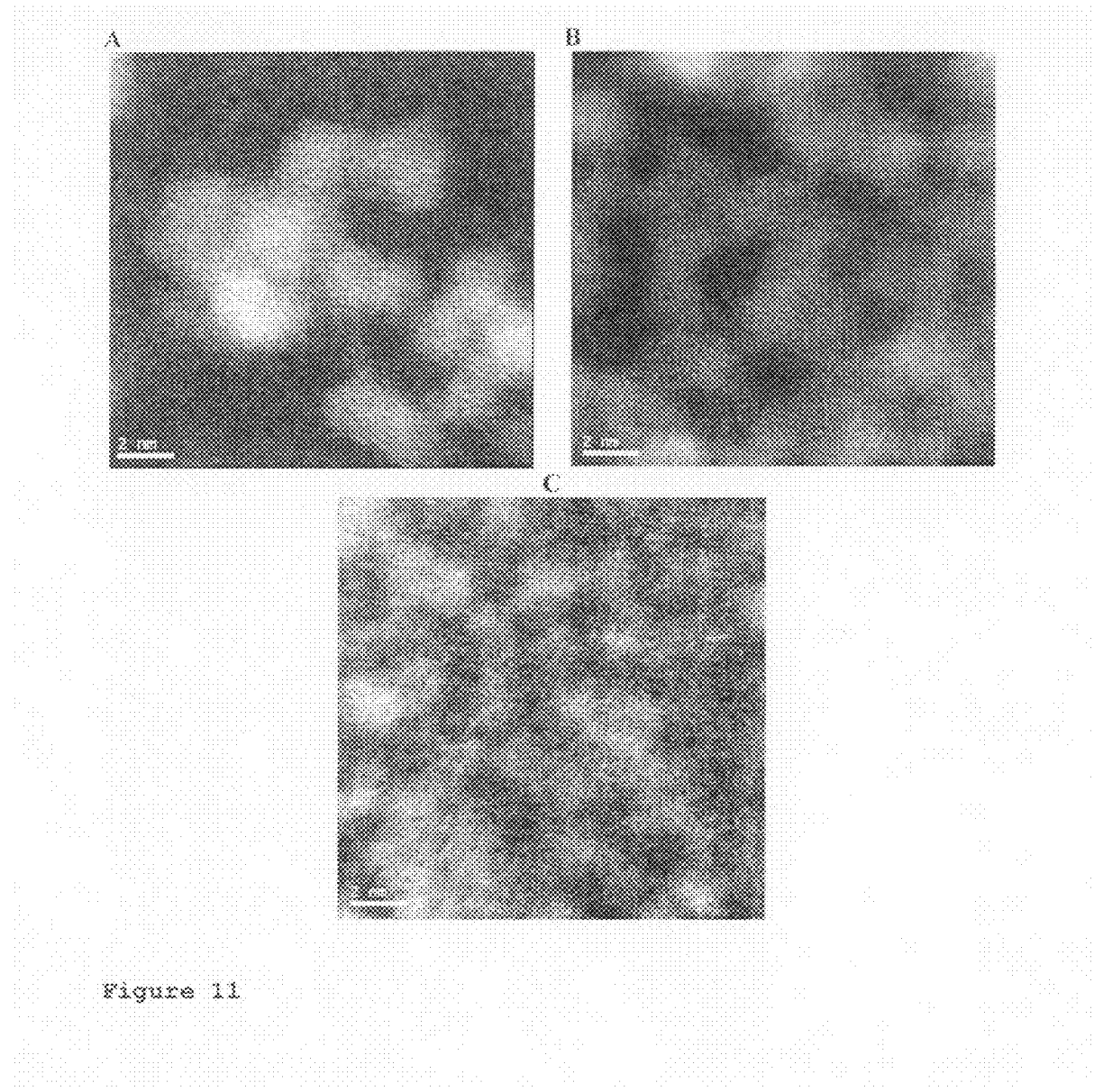
FIG. 11. Aberration corrected high angle annular dark field scanning transmission electron microscopy (superSTEM) high resolution images showing that organised, crystalline regions are less frequently discernible in ligand-modified poly oxo-hydroxy metal ion materials (e.g. FeOH-TRP15 (B) and especially in FeOHT-2:1-TRP15 (C)) than in similar sized unmodified ferric iron oxo-hydroxide (A).
Figure 12:
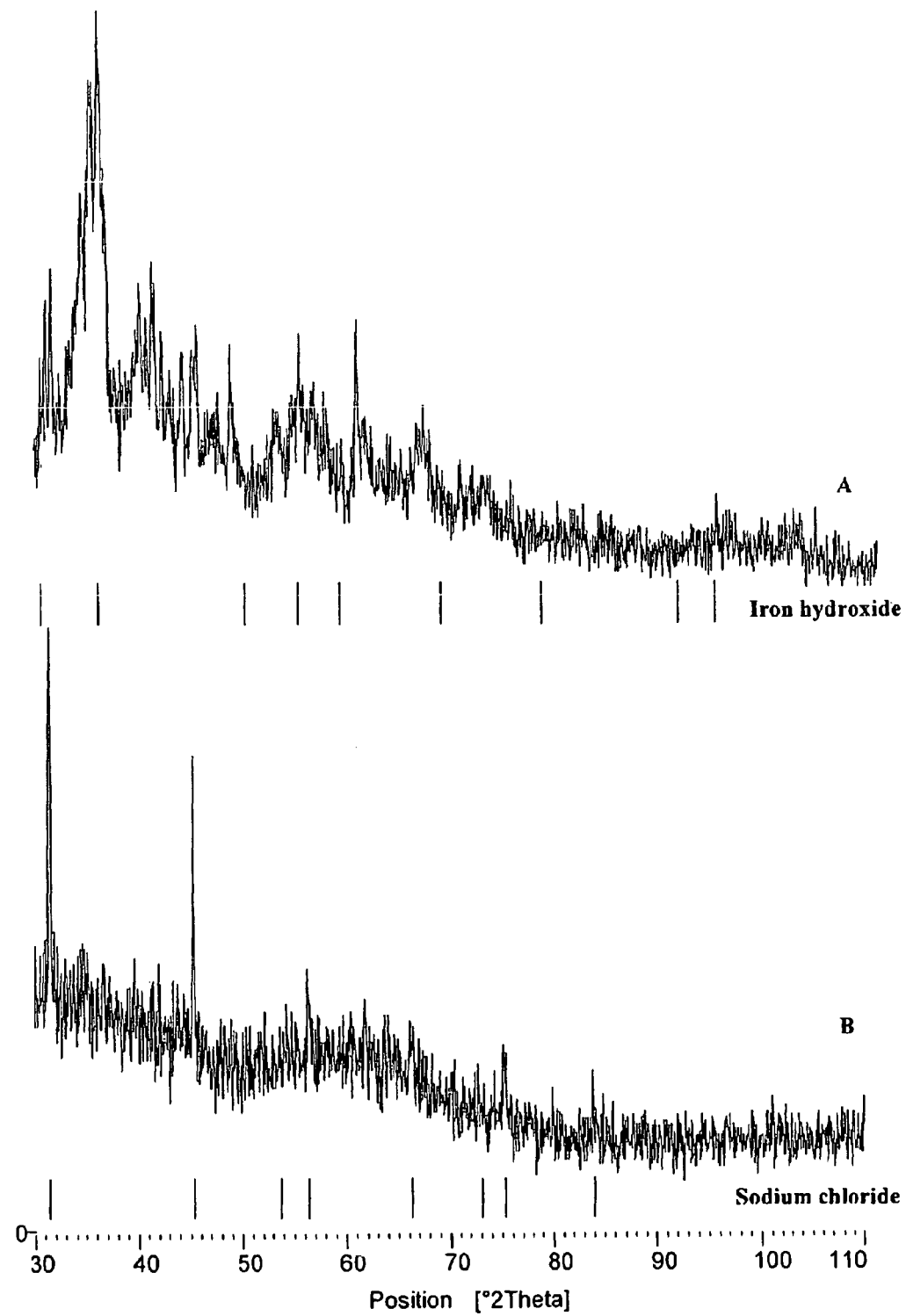
FIG. 12. X-ray diffraction pattern of Maltofer (A) and the ligand-modified poly oxo-hydroxy metal ion material FeOHT-3:1-Ad20 (B) showing a clear presence of iron oxo-hydroxide crystal structure in Maltofer and a clear lack of detectable crystalline structure in FeOHT-3:1-Ad20, apart from the co-precipitated electrolyte, sodium chloride. Reference lines for iron oxide and sodium chloride are shown below each graph for clarity.

The elemental analysis of particles from our solid ligand-modified poly oxo-hydroxy ferric iron materials measured by Energy dispersive X-ray analysis (EDX) clearly shows the presence of carbon atoms in the iron- and oxygen-containing particles (an example is shown in FIG. 8). Furthermore, the infrared spectrum of the material demonstrates the presence of a covalent-like bond between the ligand and the metal (FIG. 9) in addition to the abundant presence of hydroxy groups. This illustrates that the ligand is incorporated into the structure of the metal oxo-hydroxide lattice through formal bonding and not simply adsorption or 'entrapment'. The changes to the dissolution characteristics of the material can be readily explained by the manner in which the ligand alters the metal-oxo-hydroxide lattice. In freshly precipitated iron oxo-hydroxide a ferrihydrite-like structure is observed with some clear crystalline regions: the addition of ligand B, in this case tryptophan, reduces the extent of crystallinity while the addition of ligand A and B, in this case tryptophan and tartrate, almost negate the crystallinity entirely (FIG. 11). Maltofer, which is an organic ligand coated iron mineral particle, appeared more like freshly precipitated iron oxo-hydroxide, indicating that the ligand had not significantly modified its primary structure. This comparison is best observed using X-ray diffraction where iron hydroxide peaks are not detected for a ligand-modified poly oxo-hydroxy ferric iron material, but they are seen in Maltofer (FIG. 12) albeit broad and noisy peaks due to the very small size of the primary particles (a few nanometers).

Gastrointestinal Digestion of the Solid Ligand-Modified Poly Oxo-Hydroxy Ferric Iron Materials We compared the disaggregation of some prior art and commercial iron compounds to that of the ligand-modified poly oxo-hydroxy ferric iron materials under simulated gastrointestinal conditions (see Methods). The gastric disaggregation (pH1.2) and the gastric dissolution profiles of two of the ligand-modified poly oxo-hydroxy ferric iron materials, in comparison with ferrous sulphate, ferric oxo-hydroxide and iron polymaltose (Maltofer), are shown in FIG. 10. Ferrous sulphate disaggregates and dissolves very well at acidic pH as is expected for a metal salt. Conversely, Maltofer disaggregates very rapidly in the gastric conditions (after 5 minutes almost 80% of the iron is disaggregated) but remains in an aquated particulate form (typically around 20 nm diameter: results not shown) (FIG. 10). Percentage iron dissolution from Maltofer was less than 5% although it should be noted that there can be a loss of up to 10% of iron through binding to the ultrafiltration membrane. In comparison, the two novel ligand-modified poly oxo-hydroxy ferric iron materials had an intermediate disaggregation profile compared to ferric oxo-hydroxide and ferrous sulphate. In addition, the dissolution of these materials closely paralleled the disaggregation profile under gastric conditions although this need not be the case for these novel materials. These data show a clear difference between un-modified ferric oxo-hydroxide, Maltofer, ferrous sulfate, and our ligand-modified poly oxo-hydroxy ferric iron materials.

Disaggregation of some of our novel ligand-modified poly oxo-hydroxy ferric iron materials under gastric and intestinal conditions was also compared to dissagregation of other commercially available iron compounds, namely ferric pyrophosphate, ferric chloride, ferric trimaltol and ferrous bisglycinate. The commercial compounds either failed to disaggregate properly (e.g. ferric pyrophosphate), or they disaggregated very rapidly (FIG. 14). This rapid disaggregation, if paralleled by dissolution, is believed to be responsible for giving rise to bolus delivery of iron ions in the gut lumen and likely, therefore, the occurrence of side effects. The novel ligand-modified poly oxo-hydroxy ferric iron materials showed a degree of controlled release although, clear differences can be seen in the rates of disagreggation for the novel materials, indicating that their properties can be tailored as required (FIG. 14).

It should be noted in FIG. 14 that whether iron remains in solution or not at pH 7.0 is merely a function of whether chelators/ligands are present (as they will naturally be in the gut) and so the data for ferrous sulphate and ferric chloride (where no ligand is present in the compound) should not be over-interpreted.

Iron disaggregation and dissolution under both gastric and intestinal conditions for some ligand-modified poly oxo-hydroxy ferric iron materials that were tested further in human volunteers (see below) are presented in FIG. 15. Again we show a range of different disaggregation and dissolution profiles for the novel materials, illustrating the possibility of tailoring them as required.

Figure 17:
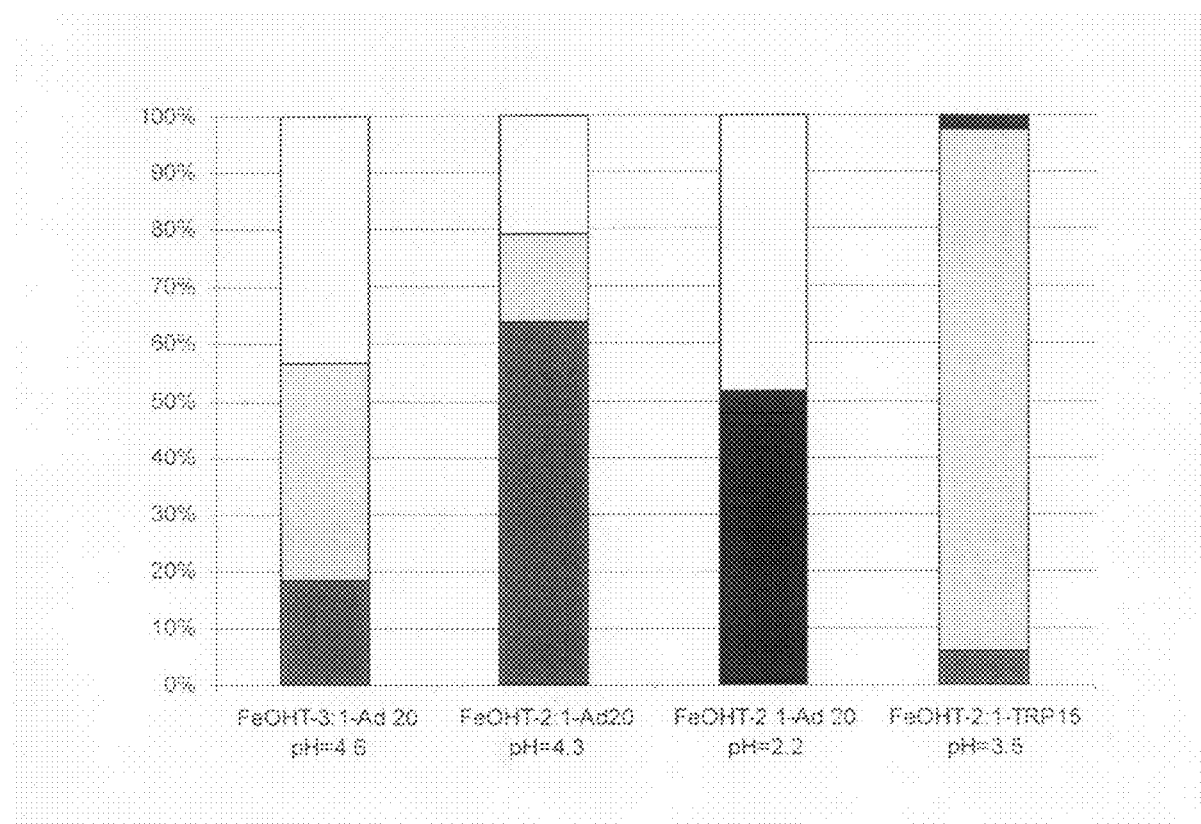
FIG. 17: Example of the effect of ligand, M:L ratio, and final solution pH of formation on the disaggregation of the tartrate-modified poly oxo-hydroxy ferric materials through the modified in vitro gastrointestinal digestion assay described in methods. Bars represent the particle size distribution of the disaggregated materials as a percentage of total iron in solid phase. Size ranges determined were <5 nm (stripped section), 5-20 nm (grey section), 20-300 nm (black section), and 1-10 μm (white section).

A study of the particle size distribution after passage through the modified gastrointestinal digestive assay of some tartrate-modified poly oxo-hydroxy ferric iron material is shown in FIG. 17. Changing the M:L ratio (first vs second bar), pH of preparation (second vs third bar) and type of ligand B (fourth bar) clearly affects the size of particles obtained and therefore disaggregation/dissolution profiles. There is especially an increase in smaller particle sizes with increasing tartrate concentrations indicating less aggregation of the primary particles with increasing L content. In addition, the higher the pH of preparation, the smaller the resulting particle size.

Iron Absorption in Humans of the Solid Ligand-Modified Poly Oxo-Hydroxy Iron Ferric Materials Seven ligand-modified poly oxo-hydroxy ferric iron materials have been assessed further for their absorption in human volunteers and the results compared with unmodified ferric oxo-hydroxide. A summary of the results is shown in Table 4.

TABLE 4

In vivo absorption of different ligand-modified poly oxo-hydroxy ferric iron materials:

| Compound | Serum Fe increase at 180 min | % absorption |
|---|---|---|
| FeOHT-3:1-Ad20 | 9 ± 3 | 5.8 ± 0.9 |
| FeOHM-4:1-Bic25 | 5.2 ± 0.6 | 1.9 ± 0.5 |
| FeOHT-2:1-Niacin50 | 3 ± 2 | 2.8 ± 0.7 |
| FeOHT-2:1-TRP15 | 8 ± 3 | 5 ± 1 |
| FeOHGluconic20 | 4.3 ± 0.5 | 6 ± 2 |
| FeOHHistidine100 | 6.0 ± 0.4 | 3 ± 2 |
| FeOHAdipate100 | 8 ± 4 | 18 ± 1 |
| FeOH | −1.3 ± 0.2* | 0.9 ± 1 |

Serum iron increase three hours after ingestion and percentage iron absorption (calculated as the red blood cell incorporation of 58Fe divided by 0.80) of solid ligand-modified poly oxo-hydroxy ferric iron materials. Mean±SEM (n ranges from 2-4); * for FeOH at 180 min there was a decrease from the baseline serum iron value.

The serum absorption profiles of the compounds (FIG. 13) show that the novel ligand-modified poly oxo-hydroxy ferric iron materials have much lower rates of iron absorption than ferrous sulphate which may be advantageous as this will prevent systemic exposure and potential damage from transiently high levels of iron. There was clear iron absorption from all formulations (FIG. 13) and for at least one preparation this is estimated to be equivalent to ferrous sulphate. It is especially noteworthy that literature reports indicate that ferric polymaltose yields no detectable rise in serum iron following ingestion and, that absorption of iron is very low (Kaltwasser et al, 1987) and would be consistent with our data for ferric oxo-hydroxide.

The compounds FeOHT-2:1-TRP15 and FeOHGluconic20 are examples of how changing the composition of these novel materials changes their serum iron profile but maintains the same percentage of iron absorption (FIG. 13) again indicating that the materials can be tailored to achieve desired outcomes.

REFERENCES

All publications, patent and patent applications cited herein or filed with this application, including references filed as part of an Information Disclosure Statement are incorporated by reference in their entirety.

Bobtelsky M and Jordan J. The structure and behaviour of ferric tartrate and citrate complexes in dilute solutions. Journal of the American Chemical Society 1947; 69:2286-2290.

Edgerton V R, Gardner G W, Ohira Y, Gunawardena K A, Senewiratne B. Iron-deficiency anaemia and its effect on worker productivity and activity patterns. British Medical Journal 1979; 2(6204):1546-1549.

Geisser P and Müller A. Pharmacokinetics of iron salts and ferric hydroxide-carbohydrate complexes. Arzneimittelforshung/Drug Research 1987; 37 (1): 100-104.

Goddard A F, James M W, McIntyre A S and Scott B B. Guidelines for the management of iron deficiency anaemia. BSG Guidelines in Gastroenterology. 2005

Harvey R S J, Reffitt D M, Doig L A, Meenan J, Ellis R D, Thompson R P H, and Powell J J. Ferric trimaltol corrects iron deficiency anaemia in patients intolerant to iron. Alimentary Pharmacology & Therapeutics 1998; 12(9):845-848.

Heinrich H C. Bioavailability of trivalent iron in oral preparations. Arzneimittelforshung/Drug Research 1975; 25(3): 420-426.

Hercberg S, Preziosi P & Galan P. Iron deficiency in Europe. Public Health Nutrition 2001; 4, 537-545.

Jugdaohsingh R, Afsharrad S, McCrohan C R, White K N, Thompson R P H and Powell J J. A rapid non-equilibrium critical precipitation assay to assess aluminium-ligand interactions. Chemical Speciation and Bioavailability 2004; 16(3):87-96.

Kaltwasser J P; Werner, E; Niechzial, M (1987). Bioavailability and therapeutic efficacy of bivalent and trivalent iron preparations. Arzneimittelforshung/Drug Research, 37(1a): 122-129.

Nielsen P, Gabbe E E, Fisher R, and Heinrich H C. Bioavailability of iron from oral ferric polymaltose in humans. Arzneimittelforshung/Drug Research 1994; 44(1): 743-748.

Powell J J, Jugdaohsingh R, Piotrowicz A, White K N, McCrohan C R and Thompson R P H. Application of the critical precipitation assay to complex samples: aluminium binding capacity of human gastrointestinal fluids. Chemical Speciation and Bioavailability 2004; 16(3):97-104.

Smith, F E; Herbert, J; Gaudin, J; Hennessy, J; Reid, G R. Serum iron determination using ferene triazine. Clinical Biochemistry 1984; 17:306-310.

Scholz B D, Gross R, Schultink W, Sastroamidjojo S. Anaemia is associated with reduced productivity of women workers even in less-physically-strenuous tasks. British Journal of Nutrition 1997; 77(1):47-57.

The invention claimed is:

1. A process for producing a solid ligand-modified poly oxo-hydroxy metal ion material $(M_xL_y(OH)_n)$, wherein M represents at least one metal ion, L represents at least one ligand and OH represents oxo or hydroxy groups, wherein the material has a polymeric structure and wherein the gross solid ligand-modified poly oxo-hydroxy metal ion material has one or more reproducible physico-chemical properties and displays M-L bonding for at least one ligand that can be detected by physical analytical techniques, the process comprising:
 (a) mixing the metal ion(s) and the ligand(s) L at a first pH(A) at which the components are soluble;
 (b) changing the pH(A) to a second pH(B) to cause a solid precipitate of the solid ligand-modified poly oxo-hydroxy metal ion material to be formed; and
 (c) separating, and optionally drying, the solid ligand-modified poly oxo-hydroxy metal ion material produced in step (b).

2. The process of claim 1, further comprising formulating the solid ligand-modified poly oxo-hydroxy metal ion material in a composition for administration to a subject.

3. The process of claim 2, wherein the step of formulating the material comprises adding an excipient.

4. The process of claim 3, wherein the composition is for use as a nutritional, medical, cosmetic or other biologically applicable composition.

5. The process of claim 1, wherein the composition is for delivery of the metal ion or the ligand to a subject.

6. The process of claim 1, wherein the composition is for sequestering or inhibiting a component present in the subject using the solid ligand-modified poly oxo-hydroxy metal ion material.

7. The process of claim 1, wherein the pH(A) is above a pH at which oxo-hydroxy polymerisation of the corresponding metal oxo-hydroxide commences.

8. The process of claim 1, wherein the pH is changed from pH(A) to pH(B) by the addition of alkali.

9. The process of claim 8, wherein the alkali is added as a solution of sodium hydroxide, potassium hydroxide or sodium bicarbonate to increase the concentration of OH in the mixture of step (b).

10. The process of claim 8, wherein pH(A) is less than or equal to pH 2 and pH(B) is greater than or equal to pH 2.

11. The process of claim 1, wherein the pH is changed from pH(A) to pH(B) by the addition of acid.

12. The process of claim 11, wherein the acid is added as a mineral acid or an organic acid to decrease the concentration of OH in the mixture of step (b).

13. The process of claim 11, wherein pH(B) is less than or equal to pH 2 and pH(A) is greater than or equal to pH 2.

14. The process of claim 1, wherein the one or more reproducible physico-chemical properties are selected from dissolution (rate, pH dependence and pM dependence), adsorption and absorption characteristics, reactivity-inertness, melting point, temperature resistance, particle size, magnetism, electrical properties, density, light absorbing/reflecting properties, hardness-softness, colour and encapsulation properties.

15. The process of claim 14, wherein the reproducible physico-chemical property is reproducible within a limit of ±10%.

16. The process of claim 1, wherein the polymeric structure in which the M, L and oxo or hydroxy groups are distributed within the solid phase structure is such that the substitution of the oxo or hydroxy groups by the one or more ligands is substantially random.

17. The process of claim 1, wherein the metal ion (M) is a Group 2, 3 or 5 metal ion, a transition metal ion, a heavy metal ion or a lanthanide ion.

18. The process of claim 17, wherein the metal ion (M) is selected from $Ag^{2+}$, $Al^{3+}$, $Au^{3+}$, $Be^{2+}$, $Ca^{2+}$, $Co^{2+}$, $Cr^{3+}$, $Cu^{2+}$, $Eu^{3+}$, $Fe^{3+}$, $Mg^{2+}$, $Mn^{2+}$, $Ni^{2+}$, $Sr^{2+}$, $V^{5+}$, $Zn^{2+}$ or $Zr^{2+}$.

19. The process of claim 17, wherein the metal ion (M) is $Fe^{3+}$.

20. The process of claim 1, wherein the ligand species (L) is selected from at least one of the carboxylic acids, adipic acid, glutaric acid, tartaric acid, aspartic acid, malic acid, succinic acid and citric acid, at least one of the food additives, maltol and ethyl maltol, at least one of the anions with ligand properties bicarbonate, sulphate and phosphate, mineral ligands, silicate, molybdate and selenate, at least one of the amino acids tryptophan, glutamine and histidine or at least one of the nutrient-based ligands folate, ascorbate and niacin.

21. The process of claim 1, wherein the ligand has buffering properties or a buffer is present in a medium for carrying out the process.

22. The process of claim 21, wherein the buffer is selected from at least one of the inorganic buffers, borate, silicate and bicarbonate, at least one of the organic buffers MOPS, HEPES, PIPES and TRIS, or at least one of the buffers, adipic acid, pimelic acid, tryptophan and hydroxymethylcellulose.

23. The process of claim 1, wherein the composition is for use an iron supplement.

24. A process for producing a solid ligand-modified poly oxo-hydroxy metal ion material and optimising a desired physico-chemical property of the material to adapt it for a nutritional, medical, cosmetic or biologically related application, wherein the solid ligand-modified poly oxo-hydroxy metal ion material is represented by the formula $(M_xL_y(OH)_n)$, wherein M represent one or more metal ions, L represents one or more ligands and OH represents oxo or hydroxy groups, wherein the material has a polymeric structure and wherein the gross solid ligand-modified poly oxo-hydroxy metal ion material has one or more reproducible physico-chemical properties and displays M-L bonding for at least one ligand that can be detected by physical analytical techniques, the process comprising:
(a) mixing the metal ion(s) M and the ligand(s) L in a reaction medium at a first pH(A) at which the components are soluble;
(b) changing the pH(A) to a second pH(B) to cause a solid precipitate of the ligand-modified poly oxo-hydroxy metal ion material to be formed;
(c) separating, and optionally drying, the solid ligand-modified poly oxo-hydroxy metal ion material produced in step (b);
(d) testing the desired physico-chemical characteristic(s) of the precipitated solid ligand-modified poly oxo-hydroxy metal ion material; and
(e) repeating steps (a) to (d) as required by varying one or more of:
(i) the identity or concentration of the metal ion(s) (M) and/or the ligand(s) (L) supplied in step (a); and/or
(ii) the ratio of metal ion(s) (M) to ligand(s) (L) supplied in (a); and/or
(iii) pH(A); and/or
(iv) pH(B); and/or
(v) the rate of change from pH(A) to pH(B); and/or
(vi) the presence or concentration of a buffer;
thereby to produce a solid ligand-modified poly oxo-hydroxy metal ion material having the desired physico-chemical property.

25. The process of claim 24, which further comprises varying a physical or chemical reaction condition used in the process for making the solid ligand-modified poly oxo-hydroxy metal ion material.

26. The process of claim 25, wherein the physical or chemical reaction condition is selected from the temperature of the reaction, the rate of pH change or the use or the conditions used to mix the reactants.

27. The process of claim 24, wherein the first pH(A) is a pH below the pH at which oxo-hydroxy polymerisation of the corresponding metal oxo-hydroxide commences.

28. The process of claim 27, wherein pH(A) is less than or equal to pH 2 and pH(B) is greater than or equal to pH 2.

29. The process of claim 24, wherein the pH is changed from pH(A) to pH(B) by the addition of acid.

30. The process of claim 29, wherein the acid is added as a mineral acid or an organic acid to decrease the concentration of OH in the mixture of step (b).

31. The process of claim 24, wherein pH(B) is less than or equal to pH 2 and pH(A) is greater than or equal to pH 2.

32. The process of claim 24, wherein the pH change from pH(A) to pH(B) occurs in a 24 hour period or less.

33. The process of claim 24, wherein the concentrations of total metal ions (M) and total ligand (L) are greater than $10^{-6}$ molar.

34. The process of claim 24, wherein the reaction medium is an aqueous solution.

35. The process of claim 24, wherein buffer stabilises the pH range of oxo-hydroxy polymerisation.

36. The process of claim 24, wherein the buffer is selected from at least one of the inorganic buffers, borate, silicate and bicarbonate, at least one of the organic buffers MOPS, HEPES, PIPES and TRIS, or at least one of the buffers, adipic acid, pimelic acid, tryptophan and hydroxymethylcellulose.

37. The process of claim 24, wherein the buffer concentrations are less than 500 mM.

38. The process of claim 24, wherein the temperature of the reaction is between 0 and 100° C.

39. The process of claim 24, wherein the ionic strength of the reaction medium is varied by addition of electrolyte.

40. The process of claim 26, wherein the components are mixed in step (a) to for a homogeneous solution.

41. A process for making a solid ligand-modified poly oxo-hydroxy metal ion material for administration to a subject, the process comprising having optimised a solid ligand-modified poly oxo-hydroxy metal ion material according to the process of claim 24 and further comprising at least one of manufacturing the solid ligand-modified poly oxo-hydroxy metal ion material in bulk and formulating said material in a composition.

42. A composition for administration to a subject comprising a solid ligand-modified poly oxo-hydroxy metal ion material represented by the formula $(M_xL_y(OH)_n)$, wherein M represents one or more metal ions, L represents one or more ligands and OH represents oxo or hydroxy groups, wherein the composition is as obtainable by the process of claim 1 and the material has a polymeric structure in which the ligands L are substantially randomly substituted for said oxo or hydroxy groups.

43. The composition of claim 42, wherein delivery of the metal ion provides therapeutic benefit to the subject.

44. The composition of claim 42, wherein the material is for use in the therapeutic removal or inhibition of an endogenous substance present in the subject that is capable of binding to the solid ligand-modified poly oxo-hydroxy metal ion material.

45. A ferric iron composition for administration to a subject which comprises a solid ligand-modified poly oxo-hydroxy metal ion material represented by the formula $(M_xL_y(OH)_n)$, wherein M represents one or more metal ions that comprise $Fe^{3+}$ ions, L represents one or more ligands and OH represents oxo or hydroxy groups and wherein the material has a polymeric structure in which the ligands L are substantially randomly, non-stoichiometrically substituted for the oxo or hydroxy groups, the solid ligand-modified poly oxo-hydroxy metal ion material having one or more reproducible physico-chemical properties and demonstrable M-L bonding using physical analysis.

46. The ferric iron composition of claim 45, wherein M is $Fe^{3+}$ ions.

47. The ferric iron composition of claim 45, wherein the solid phase structure of the material produced by the substantially random, non-stoichiometric substitution of hydroxy or oxo groups by the ligand L is determinable by an X-ray diffraction pattern having no identifiable peaks for L or MO/MOH.

48. The ferric iron composition of claim 45, wherein the solid phase structure of the material produced by the substantially random, non-stoichiometric substitution of hydroxy or oxo groups by the ligand L is an increase in the amorphousness of the structure of the material as determinable by high resolution transmission electron microscopy.

49. The ferric iron composition of claim 45, wherein the reproducible physico-chemical property is selected from one or more of a dissolution profile, an adsorption profile or a reproducible elemental ratio.

50. The ferric iron composition of claim 49, wherein the reproducible elemental ratio is reproducible within a limit of ±10%.

51. The ferric iron composition of claim 45, wherein the infrared spectra further comprises one or more peaks for the bonds between M-O, O—H, and L alone.

52. The ferric iron composition of claim 48, wherein the ligand L comprises tartarate or adipate or succinate.

53. The ferric iron composition of claim 52, wherein the ligand L comprises tartarate and adipate.

54. The ferric iron composition of claim 52, wherein the ligand L comprises tartrate and succinate.

55. The ferric iron composition of claim 48, wherein the ratio M:L is between about 1:5 and 5:1.

56. The ferric iron composition of claim 45, wherein the composition is a supplement, a fortificant or a food additive.

57. A method for therapeutic delivery of a metal ion to a subject, said method comprising administering to said subject a solid ligand-modified poly oxo-hydroxy metal ion material, prepared by the process steps of claim 1, having a polymeric structure in which the ligands are non-stoichiometrically substituted for the oxo or hydroxy groups, and said material comprising an effective amount of at least one therapeutic metal ion.

58. The method according to claim 57, wherein the solid ligand-modified poly oxo-hydroxy metal ion material administered to said subject comprises at least one therapeutic metal ion selected from the group consisting of iron, calcium, magnesium, zinc, copper, manganese, chromium and aluminium ions.

59. The method according to claim 57, wherein the therapeutic metal ions of the solid ligand-modified poly oxo-hydroxy metal ion material administered to said subject are $Fe^{3+}$ ions.

60. The method according to claim 59, wherein said material is administered for treatment of a condition selected from the group consisting of iron deficiency anemia, iron deficiency and anemia of chronic disease.

61. The method according to claim 57, wherein the solid ligand-modified poly oxo-hydroxy metal ion material is administered to said subject as a formulation further comprising a pharmaceutically acceptable carrier.

62. The method according to claim 57, wherein the solid ligand-modified poly oxo-hydroxy metal ion material is administered to said subject by a route selected from the group consisting of oral administration and intravenous administration.

63. A method of treating a subject to remove or inhibit an endogenous substance present in said subject, said substance being capable of binding to a solid ligand-modified poly oxo-hydroxy metal ion material, prepared by the process steps of claim 1, said material having a polymeric structure in which the ligands are non-stoichiometrically substituted for the oxo or hydroxy groups, said method comprising administering to said subject an amount of said material sufficient to effect binding of said material to said substance.

64. The method according to claim 63, wherein said material is administered as a phosphate binding agent.

65. The method according to claim 63, wherein the solid ligand-modified poly oxo-hydroxy metal ion material administered to said subject comprises at least one metal ion selected from the group consisting of iron, calcium, magnesium, zinc, copper, manganese, chromium and aluminium ions.

66. The method according to claim 63, wherein said solid ligand-modified poly oxo-hydroxy metal ion material is administered as a formulation further comprising a pharmaceutically acceptable carrier.

67. The method according to claim 63, wherein said solid ligand-modified poly oxo-hydroxy metal ion material is administered by a route selected from the group consisting of oral administration and intravenous administration.

68. The composition of claim 45, wherein delivery of the metal ion provides therapeutic benefit to the subject.

69. The composition of claim 45, wherein the material is for use in the therapeutic removal or inhibition of an endogenous substance present in the subject that is capable of binding to the solid ligand-modified poly oxo-hydroxy metal ion material.

* * * * *